Figure 1:
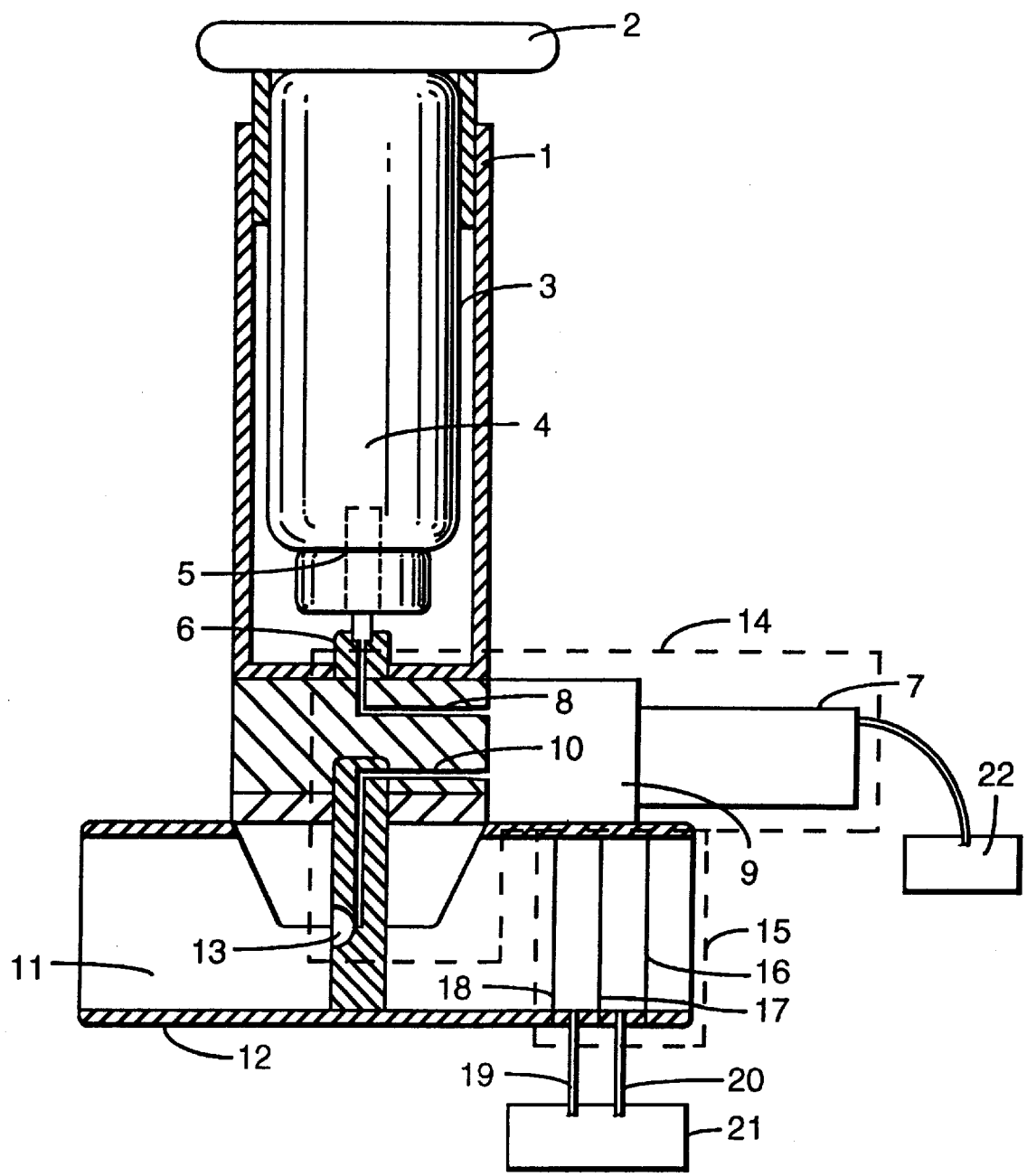

United States Patent [19]
Rubsamen

[11] Patent Number: 6,012,450
[45] Date of Patent: Jan. 11, 2000

[54] INTRAPULMONARY DELIVERY OF HEMATOPOIETIC DRUG

[75] Inventor: Reid M. Rubsamen, Berkeley, Calif.

[73] Assignee: Aradigm Corporation, Hayward, Calif.

[*] Notice: This patent is subject to a terminal disclaimer.

[21] Appl. No.: 08/673,963

[22] Filed: Jul. 1, 1996

Related U.S. Application Data

[63] Continuation of application No. 08/414,762, Mar. 31, 1995, abandoned, which is a continuation-in-part of application No. 08/330,971, Oct. 28, 1994, Pat. No. 5,558,085, which is a continuation-in-part of application No. 08/279,720, Feb. 25, 1994, Pat. No. 5,419,315, which is a continuation of application No. 08/010,989, Jan. 29, 1993, abandoned.

[51] Int. Cl.[7] ............................................ A61M 11/00
[52] U.S. Cl. ............................ 128/200.14; 128/200.23; 128/204.23; 128/203.12
[58] Field of Search ...................... 128/200.14, 200.23, 128/204.23, 205.23, 203.12

[56] References Cited

U.S. PATENT DOCUMENTS

| | | | |
|---|---|---|---|
| 3,812,854 | 5/1974 | Michaels et al. | 128/200.16 |
| 3,991,304 | 11/1976 | Hillsman | 235/151.34 |
| 4,090,642 | 5/1978 | Baker | 222/94 |
| 4,106,503 | 8/1978 | Rosenthal et al. | 128/200.18 |

(List continued on next page.)

FOREIGN PATENT DOCUMENTS

| | | |
|---|---|---|
| 0 186 280 | 10/1985 | European Pat. Off. . |
| 0 232 235 | 8/1987 | European Pat. Off. . |
| 0 232 235 A2 | 8/1987 | European Pat. Off. . |
| 2 104 393 | 3/1983 | United Kingdom . |
| 2 164 569 | 3/1986 | United Kingdom . |
| 2 255 918 | 11/1992 | United Kingdom . |
| 2 256 805 | 12/1992 | United Kingdom . |
| WO 83/04053 | 11/1983 | WIPO . |
| WO87/05813 | 10/1987 | WIPO . |
| WO90/07333 | 7/1990 | WIPO . |
| WO 91/05795 | 5/1991 | WIPO . |
| WO 91/14468 | 10/1991 | WIPO . |
| WO 92/07600 | 5/1992 | WIPO . |
| WO92/07599 | 5/1992 | WIPO . |
| WO92/07600 | 5/1992 | WIPO . |
| WO 92/09322 | 6/1992 | WIPO . |
| WO92/15353 | 9/1992 | WIPO . |
| WO92/17231 | 10/1992 | WIPO . |
| WO 93/17728 | 9/1993 | WIPO . |
| WO 94/20069 | 9/1994 | WIPO . |

OTHER PUBLICATIONS

Newman et al., 1981. "How Should a Pressurized Beta–Adrenergic Bronchodilator be Inhaled?" *Eur. J. Respir. Dis.* 62:3–21.

(List continued on next page.)

*Primary Examiner*—Aaron J. Lewis
*Attorney, Agent, or Firm*—Karl Bozicevic; Bozicevic & Reed

[57] ABSTRACT

A method of treating human patients is provided by the intrapulmonary delivery of a formulation containing a hematopoietic drug. The formulation is automatically released in an aerosolized form from a hand-held, self-contained, portable device comprised of a means for automatically releasing a measured amount of drug into the inspiratory flow path of a patient in response to information obtained from a means for measuring the inspiratory flow rate and determining the inspiratory volume of a patient. Reproducible dosing is obtained by providing for automatic release at the same inspiratory flow rate and inspiratory volume each time drug is released. The device includes a timer to enable a patient to take a drug at the same time each day. Further, overadministration of a hematopoietic drug formulation is avoided by providing a pre-programmed microprocessor designed to avoid overdosing.

18 Claims, 7 Drawing Sheets

U.S. PATENT DOCUMENTS

| | | | |
|---|---|---|---|
| 4,179,337 | 12/1979 | Davis et al. | 435/181 |
| 4,361,401 | 11/1982 | Smith et al. | 356/36 |
| 4,604,847 | 8/1986 | Moulding, Jr. et al. | 53/75 |
| 4,627,432 | 12/1986 | Newell et al. | 128/203.15 |
| 4,677,975 | 7/1987 | Edgar et al. | 128/200.14 |
| 4,686,231 | 8/1987 | Bender et al. | 514/333 |
| 4,819,629 | 4/1989 | Jonson | 128/203.22 |
| 4,877,989 | 10/1989 | Drews et al. | 310/32.3 |
| 4,926,852 | 5/1990 | Zoltan | 128/200.23 |
| 4,934,358 | 6/1990 | Nilsson et al. | 128/200.23 |
| 4,984,158 | 1/1991 | Hillsman | 128/725 |
| 5,011,678 | 4/1991 | Wang et al. | 424/45 |
| 5,013,718 | 5/1991 | Adamson et al. | 514/8 |
| 5,167,506 | 12/1992 | Kilis et al. | 434/262 |
| 5,284,656 | 2/1994 | Platz et al. | 424/435 |
| 5,354,934 | 10/1994 | Pitt el al. | 514/8 |
| 5,363,842 | 11/1994 | Mishelevich et al. | 128/200.14 |
| 5,392,768 | 2/1995 | Johansson et al. | 128/200.14 |
| 5,394,866 | 3/1995 | Ritson et al. | 128/200.14 |
| 5,419,315 | 5/1995 | Rubsamen | 128/200.23 |

OTHER PUBLICATIONS

Yoshida et al., "Absorption of Insulin Delivered to Rabbit Trachea Using Aerosol Dosage Form", *Journal of Pharmaceutical Sciences,* 68(5):670–671 (1979).

Kohler, "Aerosols for Systemic Treatment", *Lung,* Suppl:677–684 (1990).

Laube et al., "Aerosolized Insulin Delivered Through the Lungs is effective in Normalizing Plasma Glucose Levels in Non–Insulin Dependent Diabetic Subjects", *Journal of Aerosol Medicine* 4(3):286 (1991).

Colthorpe et al., "The Pharmacokinetics of Pulmonary–Delivered Insulin: A Comparison of Intratracheal and Aerosol Administration to the Rabbit", *Pharmaceutical Research,* 9(6):764–768 (1992).

Jaffe et al., "Rats Self–Administer Sufentanil Aerosol Form", *Psychopharmacology,* 99:289–293 (1989).

Smythe, "Patient–Controlled Analgesia: A Review", *Pharmacotherapy,* 12(2):132–143 (1992).

Shade, "Patient–Controlled Analgesia: Can Client Education Improve Outcomes?", *Journal of Advanced Nursing,* 17:408–413 (1992).

Camp, "Patient–Controlled Analgesia", *AFP,* 44(6):2145–2150 (1991).

Mather, "Pharmacokinetics and Patient–Controlled Analgesia", *Acta Anaesthesiologica Belgica,* 43(1):5–20 (1992).

Ryder, "All About Patient–Controlled Analgesia", *Journal of Intravenous Nursing,* 14(6):372–381 (1991).

Rosenberg, "Patient–Controlled Analgesia", *J. Oral Maxillofac. Surg.,* 50:386–389 (1992).

Newman, *Deposition and Effects of Inhalation Aerosols* (2nd ed.), Churchill Livingstone (1983).

Gourlay et al., "Fentanyl Blood Concentration–Analgesic Response Relationship in the Treatment of Postoperative Pain", *Anesth. Analg.,* 67:329–337 (1988).

Miller, *Anesthesia* (2nd ed.), Churchill Livingstone, 1:762 (1986).

Rapp et al., "Patient–Controlled Analgesia: A Review of Effectiveness of Therapy and an Evaluation of Currently Available Devices", *DICP, The Annals of Pharmacotherapy,* 23:899–904 (1989).

Rowbotham et al., "A Disposable Device for Patient–Controlled Analgesia with Fentanyl", *Anaesthesia,* 44:922–924 (1989).

Lehmann et al., "Transdermal Fentanyl for the Treatment of Pain after Major Urological Operations", *Eur. J. Clin. Pharmacol.* 41:17–21 (1991).

Newman et al., "Deposition of Pressurised Aerosols in the Human Respiratory Tract", *Thorax,* 36:52–55 (1981).

Nieminen et al., "Aerosol Depostion in Automatic Dosimeter Nebulization", *Eur. J. Respir. Dis.,* 71:145–152 (1987) and.

Newman et al., "How Should a Pressurized β–adrenergic Bronchodilator be Inhaled?", *Eur. J. Respir. Dis.,* 62:3–21 (1981).

Adjei et al., "Pulmonary Delivery of Peptide Drugs: Effect of Particle Size of Bioavailability of Leuprolide Acetate in Healthy Male Volunteers", *Pharmaceutical Research,* 7(6):565–567.

Wearley, "Recent Progress in Protein and Peptide Delivery by Noninvasive Routes", *Critical Reviews in Therapeutic Drug Carrier Systems,* 8(4):331–392.

Salzman et al., "Intranasal Aerosolized Insulin", *New England Journal of Medicine,* 213(17:1078–1084 (1985).

Wigley et al., "Insulin Across Respiratory Mucosae by Aerosol Delivery", *Diabetes,* 20(8):552–556 (1971).

Adjei A. et al., "Bioavailability of leuprolide following intratracheal administration to beagle dogs", 1990, International Journal of Pharmaceutics, 61:135–144.

Barrowcliffe, M. et al., "Pulmonary clearance of vasoactive intestinal peptide", 1986, Thorax 41:88–93.

Braquet, P., "Effect of endothelin–1 on blood pressure and bronchopulmonary system of the guinea pig", 1989, Journal of Cardiovascular Pharmacology, 13(Suppl. 5):S143–S146.

Camp, J., "Patient–controlled analgesia", 1991, AFP, 44:2145–2150.

Colthorpe, P. et al., "The Pharmacokinetics of Pulmonary––Delivered Insulin: A Comparison of Intratracheal and Aerosol Administration to the Rabbit", 1992, Pharmaceutical Research, 9:764–768.

Debs, R. et al., "Lung–specific delivery of cytokines induces sustained pulmonary and systemic immunomodulation in rats", 1988, Journal of Immunology, 140:3482–3488.

Gourlay, G.K., "Fentanyl Blood Concentration–Analgesic Response Relationship in the Treatment of Postoperative Pain", 1988, Anesth. 67:329–337.

Harrison, T.R. et al., Harrison's Principles of Internal Medicine (10th edition), 1983, pp. 666–674.

Hubbard, R.C. et al., "Anti–neutrophil–Elastase Defenses of the Lower Respiratory Tract in a1–Antitrypsin Deficiency Directly Augmented with an Aerosol of a1–Antitrypsin", Annals of Internal Medicine, 111:206–212.

Hubbard, R.C. et al., "Fate of aerosolized recombinant DNA–produced a1–antitrypsin:Use of the epithelial surface of the lower respiratory tract to administer proteins of therapeutic importance", 1989, Proc. Natl. Acad. Sci. USA 86:680–684.

Jaffe, A.B., et al., "Rats self–administer Sufentanil in Aerosol Form", 1989, Psychopharmacology, 99:289–293.

Kohler, D., "Aerosols for Systemic Treatment", 1990, Lung, Suppl.:677–684.

Laube, Beth L. et al., "Aerosolized Insulin Delivered Through The Lungs Is Effective In Normalizing Plasma Glucose Levels In Non–Insulin Dependent Diabetic Subjects", 1991, J. Aerosol Medicine, 4:286.

Laube, Beth L., "Preliminary Study of the Efficacy of Insulin Aerosol Delivered by Oral Inhalation in Diabetic Patients", 1993, JAMA 269:2106–2109.

Lee, V.H., "Changing Needs in Drug Delivery in the Era of Peptide and Protein Drugs", Marcel Dekker, N.Y., pp. 1–11.

Lehman, K.A. et al., 1991, "Transdermal Fentanyl for the Treatment of Pain After Major Urological Operations", Eur. J. Clin. Phamacol. 41:17–21.

Mather, L.E., "Pharmacokinetics and Patient–Controlled Analgesia(*)", 1992, Acta Anaesthesiologica Belgica, 43:5–20.

Miller, R., "Anesthesia Second Edition", 1986, Churchill Livingstone, 1:762.

Moses et al., Insulin Administered Intranasally as an Insulin– Bile Salt Aerosol—Effectiveness and Reproductibility in Normal and Diabetic Subjects, 1983, Diabets 32:1040–1047.

Newman, S.P. et al., "How should a pressurized β–adrenergic bronchodilator be inhaled?", 1981, Eur. J. Respir. Dis. 62:3–21.

Newman, S.P. et al., "Deposition of pressurized suspension aerosols inhaled through extension devices", 1981, Am. Rev. Respir. Dis. 124:317–320.

Newman, S.P. et al., "Deposition of Pressurized Aerosols in the Human Respiratory Tract", 1981, Thorax, 36:52–55.

Newman, S.P. et al., "Deposition and Effects of Inhalation Aerosols", 1983, Dept. of Thoracic Medicine.

Nieminen et al., "Aerosol Deposition in Automatic Dosimeter Nebulization" 1987, European Journal of Respiratory Diseases, 71:145–152.

Patton, J.S. et al., "Routes of Delivery: Case Studies–Pulmonary delivery of peptides and proteins for systemic action", 1992, Advanced Drug Delivery Reviews, 8:179–196.

Rapp, R.P. et al., Patient–controlled analgesia:a review of effectiveness of therapy and an evaluation of currently available devices, 1989, DICP, The Annals of Pharmacotherapy 23:899–904.

Rosenberg, M., "Patient–Controlled Analgesia", 1992, J. Oral Maxillofac. Surg. 50:386–389.

Rowbotham, D.J., "A disposable device for patient–controlled analgesia with fentanyl", 1989, Anaesthesia, 44:922–924.

Ryder, E., "The history of patient–controlled analgesia", 1991, Journal of Intravenous Nursing, 14(6):372–381.

Salzman, R., et al., Intranasal Aerosolized Insulin Mixed–Meal Studies and Long–Term Use in Type I Diabetes, 1985, New England Journal of Medicine, 213:1078–1084.

Shade, P., "Patient–controlled Analgesia: Can Client Education Improve Outcomes?", 1992, Journal of Advanced Nursing, 17:408–413.

Smith, Robert M., et al., "Pulmonary Deposition and Clearance of Aerosolized Alpha–1–Proteinase Inhibitor Administered to Dogs and to Sheep", 1989, J. Clin. Invest. 84:1145–1154./

Smythe, M., "Patient–controlled Analgesia:A Review", 1992, Pharmacotherapy, 99:289–293.

Wearley, Lorraine L., "Recent Progress in Protein and Peptide Delivery by Noninvasive Routes", 1991, Critical Reviews in Therapeutic Drug Carrier Systems, 8:331–392.

Wigley, F.M. et al., "Insulin Across Respiratory Mucosae by Aerosol Delivery" 1971, Diabetes, 20:552–556.

Dexter et al., *BioEssays* 2:154–158 (1985).

Lin et al., "Monkey Erythropoietin Gene: Cloning, Expression and Comparison With the Human Erythropoitin Gene" *Gene* 44:201–209 (1986).

McDonald et al., "Cloning, Sequencing, and Evolutionary Analysis of the Mouse Erythropoietin Gene" *Molecular and Cellular Biology* 6:842–848 (1986).

Delwell et al., "Growth Regulation of Human Acute Myeloid Leukemia: Effects of Five Recombinant Hematopoietic Factors in a Serum–Free Culture System" *Blood* 72:1944–1949 (1988).

Spangrude et al., "Purification and Characterization of Mouse Hematopoietic Stem Cells" *Science* 241:58–62 (1988).

Lee et al., "Alteration of Terminal Glycosylation Sequences on N–Linked Oligosaccharides of Chinese Hamster Ovary Cells by Expression of β–Galactoside α2,6–Sialytransferase" *J. Biolog. Chem.* 264:13848–13855 (1989).

Wide and Bengtsson, "Molecular Charge Heterogeneity of Human Serum Erythropoietin" *British Journal of Haematology* 76:121–127.

Storring and Das, "The International Standard for Recombinant DNA–derived Erythropoietin: Collaborative Study of Four Recombinant DNA–Derived Erythropoietins and Two Highly Purified Human Urinary Erythropoietins" *J. Endocrin.* 134:459–484 (1992).

Strickland et al., *J. Cell. Biochem.*, suppl. 16D, p. 324 (1992).

"Recent Progress in Protein and Peptide Delivery by Noninvasive Routes", By Wearley, Critical Reviews in Therapeutic Drug Carrier Systems, 8(4):331–394 (1991).

"How Should A Pressurized B–Adrenergic Bronchodilator Be Inhaled?", by Newman et al., Eur. J. Respir. Dis., 62, 3→21, (1981).

INTRAPULMONARY DELIVERY OF HEMATOPOIETIC DRUG

CROSS REFERENCE TO RELATED APPLICATIONS

This is a continuation of application Ser. No. 08/414,762, filed on Mar. 31, 1995, now abandoned, which is a continuation-in-part of application Ser. No. 08/330,971, filed Oct. 28, 1994, now U.S. Pat. No. 5,558,085, which is a continuation in part of application Ser. No. 08/279,720, filed Jul. 25, 1994 now U.S. Pat. No. 5,419,315, issued May 30, 1995, which is a continuation of application Ser. No. 08/010,989, filed Jan. 29, 1993, now abandoned.

This application is a continuation-in-part of our earlier filed application Ser. No. 08/330,971 filed Oct. 28, 1994 which application is a continuation-in-part of earlier filed application Ser. No. 08/279,720 filed Jul. 25, 1994 which is a file-wrapper-continuation application of application Ser. No. 08/010,989 filed Jan. 29, 1993 which applications are incorporated herein by reference and to which applications is claimed priority under 35 USC §120. This application is also a continuation-in-part of U.S. application Ser. No. 08/011,245, filed Jan. 29, 1993 which is a continuation-in-part of application Ser. No. 07/664,758, filed Mar. 5, 1991 to which applications we claim priority under 35 USC §120 and which applications are incorporated herein by reference.

FIELD OF THE INVENTION

This invention relates generally to methods of administering compounds which effect erythropoiesis. More specifically, this invention relates to the intrapulmonary delivery of compounds from a hand-held, self-contained device which automatically and repeatedly releases a controlled amount of a drug to a patient at the same point in the respiratory cycle of the patient based on both inspiratory flow rate and inspiratory volume so as to obtain a high degree of efficiency in delivery and repeatability in dosing.

BACKGROUND OF THE INVENTION

Drugs are available which enhance the activity of a hematopoietic (bloodforming) system. Such a system replenishes the multiplicity of blood cell types found in a healthy animal, including white blood cells (neutrophils, macrophages, and basophil/mast cells), clot forming cells (megakaryocytes, platelets), and red blood cells (erythrocytes).

The average human male's hematopoietic system has been estimated to produce on the order of $4.5 \times 10^{11}$ granulocytes and erythrocytes every year, which is equivalent to an annual replacement of total body weight [Dexter et al., (1985) *BioEssays*, vol. 2:154–158]. Current scientific understanding proposes that small amounts of specific hematopoietic growth factors direct the proliferation, differentiation, and maturation of each of the various hematopoietic cell types from a small population of pluripotent hematopoietic stem cells. These various growth factors act at different times on different cell populations, ultimately giving rise to a functional hematopoietic system. Drugs such as erythropoietin enhance the production of erythrocytes, or red blood cells, which transport oxygen to the various tissues of the animal's body. The process of producing erythrocytes ("erythropoiesis") occurs continuously throughout an animal's life span to offset erythrocyte destruction. The typical red blood cell has a relatively short life-span, usually 100 to 120 days; *Gray's Anatomy*, Williams et al. eds., Churchill Livingstone, 1989, p. 665. Erythropoiesis is a precisely controlled physiological mechanism whereby sufficient numbers of erythrocytes are produced to enable proper tissue oxygenation, but not so many as to impede circulation.

Erythropoietin (EPO) is a hormone or more specifically a peptide hormone largely produced in the peritubular interstitial cells of the kidneys. EPO is produced as the result of the expression of a single copy gene. A DNA molecule encoding a DNA sequence for human EPO has been isolated and is described in U.S. Pat. No. 4,703,008, hereby incorporated by reference, and hereinafter referred to as the '008 patent." Also, DNA molecules coding for EPO from monkeys [Lin et al., (1986) *Gene*, vol. 44, pp: 201–209] and mice [McDonald et al., (1986) *Mol. Cell Biol.*, pp: 842] have been described. The amino acid sequence for recombinant human EPO ("rHuEPO") is identical to the sequence for EPO obtained from human urinary sources. However, as could be expected, the glycosylation of rHuEPO differs from that of urinary EPO and human serum EPO. See, e.g. Starring et al. (1992), *J. Endocrin.*, vol. 134, pp: 459–484; Strickland et al. (1992), *J. Cell. Biochem.*, suppl. 16D, p. 324; Wide et al. (1990), *Br. J. Haematol.*, vol. 76, 121–127.

EPO is normally present in the blood plasma in very low concentrations, as the tissues are being sufficiently oxygenated by the existing number of circulating erythrocytes. The EPO present stimulates the production of new erythrocytes to replace those lost to the aging process. Additionally, EPO production is stimulated under conditions of hypoxia, wherein the oxygen supply to the body's tissues is reduced below normal physiological levels despite adequate perfusion of the tissue by blood. Hypoxia may be caused by hemorrhaging, radiation-induced erythrocyte destruction, various anemias, high altitude, or long periods of unconsciousness. In contrast, should the number of red blood cells in circulation exceed what is needed for normal tissue oxygenation. EPO production is reduced.

Recombinant human EPO (rHuEPO) is being used therapeutically in a number of countries. In the United States, the U.S. Food and Drug Administration (FDA) has approved rHuEPO's use in treating anemia associated with end-stage renal disease. Patients undergoing hemodialysis to treat this disorder typically suffer severe anemia, caused by the rupture and premature death of erythrocytes as a result of the dialysis treatment. EPO is also useful in the treatment of other types of anemia. For instance, chemotherapy-induced anemia, anemia associated with myelodysplasia, those associated with various congenital disorders, AIDS-related anemia, and prematurity-associated anemia, may be treated with EPO. Additionally, EPO may play a role in other areas, such as helping to more quickly restore a normal hematocrit in bone marrow transplantation patients, in patients preparing for autologous blood transfusions, and in patients suffering from iron overload disorders. See e.g. U.S. Pat. No. 5,013,718, hereby incorporated by reference.

The effective use of EPO as a therapeutic agent requires that patients be administered small but highly precise doses of the protein in stable, pharmaceutically acceptable formulations. For an example of a current EPO formulation, see Sobata, J., *Erythropoietin in Clinical Applications*, Garnick, M., ed. Marcel Dekker, Inc., New York (1990). Current therapy for end-stage renal disease calls for intravenous EPO administration within twelve hours of dialysis, three times a week. Alternatively, EPO may be administered to such patients by intravenous, intramuscular, intracutaneous, or subcutaneous injection. U.S. Pat. No. 5,354,934 (incorporated herein by reference) shows that a nebulizer can deliver EPO to the circulatory system of a rat.

The instant invention is based upon the unexpected discovery that EPO may be efficiently and accurately administered by inhalation in a therapeutically efficacious manner by a small self-contained hand-held device. EPO delivered to the lung in this manner is absorbed into the patient's bloodstream for systemic distribution. This new route of EPO administration enables the rapid delivery of a specified medicament dosage to a patient without the necessity for injection. In addition, pulmonary administration more readily lends itself to self-administration by the patient.

There has been some prior success in the pulmonary administration of pharmaceutical compositions comprised of hormones. Hormones such as EPO are currently administered by injection. Because the stomach presents a highly acidic environment, oral preparations of peptides are unstable and readily hydrolyzed in the gastric environment. Currently, there are no oral preparations of EPO or any other therapeutic peptide agents available.

Both calcitonin and leuprolide can be administered nasally. (See Rizzato et al., *Curr. Ther. Res.* 45:761–766, 1989.) Both drugs achieve blood levels when introduced into the nose from an aerosol spray device. However, experiments by Adjei et al. have shown that the bioavailability of leuprolide when administered intranasally is relatively low. Adjei and Garren, *Pharmaceutical Research*, Vol. 7, No. 6, 1990.

An increase in the bioavailability of leuprolide can be obtained by administering the drug into the lung. Intrapulmonary administration of leuprolide has been shown to be an effective means of non-invasive administration of this drug. Adjei and Garren, *Pharmaceutical Research*, Vol. 7, No. 6, 1990. Intrapulmonary administration of leuprolide and other peptide drugs has the additional advantage of utilizing the large surface area available for drug absorption presented by lung tissue. This large surface area means that a relatively small amount of drug comes into contact with each square centimeter of lung parenchyma. This fact reduces the potential for tissue irritation by the drug and drug formulation. Adjei et al., demonstrated that peptide drugs could be successfully delivered to a patient by the intrapulmonary route without the need for any permeation enhancers. Local irritation has been seen with nasal delivery of insulin and has been a problem for commercialization of nasal preparations of that drug.

Hormones such as leuprolide and EPO are very potent with effects that are not immediately manifested. For example, therapy with leuprolide for prostrate cancer does not typically produce any acute clinical effects. Similarly, prophylaxis against osteoporosis with calcitonin will not produce any acute symptoms discernible to the patient. Therefore, administration of each dose of these drugs must be reliable and reproducible. Careful compliance monitoring is important to avoid therapeutic failures by carefully following the patient's adherence to the prescribed dosing regiment. In addition, because these drugs are potent therapeutic agents, care must be taken to avoid overdosing.

Pulmonary administration of α-1-proteinase inhibitor to dogs and sheep has been found to result in passage of some of that substance into the bloodstream. See Smith et al., *J. Clin. Invest.*, vol. 84, pp. 1145–1154 (1989). Likewise, aerosolized α-1 anti-trypsin diffused across the lung epithelium and entered into systemic circulation in sheep and humans. See Hubbard et al., (1989) *Ann. Intern. Med.*, vol. 111, pp. 206–212.

Experiments with test animals have shown that recombinant human growth hormone, when delivered by aerosol, is rapidly absorbed from the lung and produces faster growth comparable to that seen with subcutaneous injection. See Oswein et al., "*Aerosolization of Proteins*", Proceedings of Symposium on Respiratory Drug Delivery II, Keystone, Colo., March, 1990. Recombinant versions of the cytokines gamma interferon (IFN-γ) and tumor necrosis factor alpha (TNF-α) have also been observed in the bloodstream after aerosol administration to the lung. See Debs et al., *The Journal of Immunology*, Vol. 140, pp. 3482–2388 (1988). Likewise, Pitt et al. have recently demonstrated the feasibility of pulmonary delivery of granulocyte-colony stimulating factor (G-CSF) to mammals. See published PCT application WO94/20069 published Sep. 15, 1994 and incorporated herein by reference.

The lungs contain $3 \times 10^8$ alveoli with a total surface area of approximately 140 $m^2$. Alveoli are thin walled pouches that represent as minimal a barrier to gaseous exchange between the atmosphere and blood as is possible without comprising the integrity of the lung. Correspondingly, capillary beds adjacent to the alveoli are estimated to share a surface area of 125 $m^2$ with the alveoli [*Gray's Anatomy*, supra]. Thus, each alveolus is in intimate association with numerous blood-bearing capillaries bringing oxygen-depleted blood from distal body tissues.

Based on the above cited publications it can be seen that the pulmonary delivery of many types of peptide drugs is known. By administering large amounts of an aerosolized drug containing formulation a therapeutic level of the drug in the circulatory system can be obtained. For example, a nebulizer can be used and the subject can breath aerosolized formulation from the nebulizer for a long enough period to obtain a therapeutically effective level. However, such a procedure is not only inefficient it does not allow for precise dosing.

The most convenient form for intrapulmonary administration of drugs by ambulatory patients is through the use of a metered dose inhaler. Metered dose inhaler devices allow the self-administration of a metered bolus of drug when the device is manually actuated by the patient during inspiration. However, such devices must be used with the proper inspiratory maneuver in order to promote effective deposition of the drug into the lung. In addition to performing a correct inspiratory maneuver, the patient must self-actuate the metered dose inhaler during the appropriate part of the inspiratory cycle. Further, when using such devices, it is not typically self-evident to the patient that the drug was properly or improperly administered. For those drugs without immediate clinical effect, the patient can easily misuse the metered dose inhaler and be under the false impression that he is correctly self-administering the drug as prescribed. Similarly, the patient may be under the false impression that he performed an incorrect inspiratory maneuver in metered dose inhaler actuation when he in fact properly performed these operations and received an appropriate amount of drug.

Devices exist to deliver metered dose inhaler drugs into the lung in a breath-actuated manner. However, such devices do not measure inspiratory flow rate and determine inspiratory volume in order to trigger the device. Therefore, a sub-optimal inspiratory maneuver (e.g. one with too high of an inspiratory rate) could be used to actuate the device and produce a sub-optimal deposition pattern of drug into the lungs resulting in a sub-therapeutic blood level of the therapeutic agent being delivered. If delivery took place at the correct point in the inspiratory cycle the dose delivered would be high—overall dosing would be erratic in that drug is released at different points in the inspiratory cycle.

When using a metered dose inhaler, the dosing events must be manually recorded by the patient. Many potent therapeutic hormone peptide drugs are given only once a day. It is important that the patient remember to take the prescribed daily dose, and that the dose be taken at the correct time of the day. Further, it is important that the patient not take more than the prescribed number of doses per day. The timing of delivery of potent therapeutic hormone peptide drugs is critical because these drugs interact intimately with the chronobiology of the patient's physiology in order to produce their desired effect.

When using standard metered dose inhaler devices, the patient must manually record the time of each dosing administration. In addition, the patient must remember when to self-administer the drug. Devices exist for recording automatically metered dose inhaler drug delivery events. However, such devices do not record the presence of inspiratory flow at the time of device firing. This means that a noncompliant patient can fire the metered dose inhaler into the air and have a valid drug dosing event recorded on the self-containing recording means. In addition, the patient could self-administer the drug with an inappropriate inspiratory maneuver and have a valid drug dosing event recorded by the device. This would lead the physician to assume that the patient was compliant when he was receiving an inappropriate amount of drug with each dosing event.

The present invention endeavors to provide an efficient method for the pulmonary delivery of EPO to a patient in a manner such that dosing is closely controlled and administration is from a convenient, hand-held device.

SUMMARY OF THE INVENTION

A method of treating the hematopolitic system of a mammal is provided by the intrapulmonary delivery of a pharmaceutically active formulation of a hematopoietic drug (as defined herein) which enhances the level of red blood cells in a therapeutically recognizable amount. The formulation is automatically released in an aerosolized form from a hand-held, self-contained, portable device comprised of a means for automatically releasing a measured amount of drug into the inspiratory flow path of a patient in response to information obtained from a means for measuring the inspiratory flow rate and determining the inspiratory volume of a patient. Reproducible dosing and efficient administration are obtained by providing for automatic release at the same inspiratory flow rate and inspiratory volume (determined in real time) each time drug is released. The methodology involves measuring for, determining and/or calculating a firing point or drug release decision based on instantaneously (or real time) calculated, measured and/or determined inspiratory flow rate and inspiratory volume points. The device delivers 20% or more of the aerosolized drug to the circulatory system of the patient. The device includes a timer to enable a patient to take a drug at the same time each day. The formulation is preferably aerosolized by moving the formulation through a porous membrane having pores which are about 0.5 to 6.0 microns in diameter. Further, overadministration of hematopoietic formulations is avoided by providing a pre-programmed microprocessor designed to avoid overdosing. The device and methodology make it possible to improve the efficiency of treatment with a hand-held device in three ways: (1) the point of release considers both inspiratory flow and volume (2) the potency of the hematopoietic drug used can be very high (i.e., in terms of the number of units per mg and in terms of the concentration i.e., mg/ml of formulation); (3) potency can be improved several fold by using particular synergistic combinations of drugs; and (4) all of 1–3 can be used due to the repeatability in dosing which can be obtained.

It is an object of this invention to provide a method of aerosolized delivery of a therapeutically effective amount of a hematopoietic drug in an efficient reproducible, safe and effective manner.

An advantage of the method and device is that 20% or more of the aerosolized drug released enters the circulatory system of the patient making it possible to treat the hematopoietic system using a hand-held device.

Another advantage of the present invention is that it can be used for ambulatory patients.

It is a feature of the invention that the device used for the aerosolized delivery of hematopoietic drug formulations records the time and amount of formulation delivered.

Another advantage of the present invention is that the device used for delivering hematopoietic drug formulations includes a timer which emits an audible and/or visual signal to the patient at each scheduled dosing event.

Yet another advantage of the present invention is that the method involves administering hematopoietic drug formulations while simultaneously keeping an index which corresponds to the quality of the patient's inspiratory flow profile at each dosing event.

Another feature of the present invention is that when carrying out the method of delivery, a record of the date and time of each dosing event is electronically and automatically produced within a unitary, hand held device which delivers the drug.

Another advantage of the present invention is that the device presents a visual display calendar which calendar specifically indicates to the patient the day and/or time a dose was administered.

Another feature of the present invention is that the device for administering drug includes a microprocessor programmed to prevent the administration of more doses than are prescribed for the particular deficiency being treated.

Another advantage of the present invention is that better treatment protocols can be developed by the treating physician by transferring information from the delivery/recording device to a printout device which can be reviewed in order to determine the complete compliance history of the patient.

Another object of this invention is to provide an apparatus which can analyze the breathing pattern of the patient and can measure the respiratory flow rate and measure the inspiratory volume at the same time in order to determine an optimal point in the inspiratory cycle for delivery of aerosolized hematopoietic drug.

Another advantage is that the method described provides for reproducible delivery of hematopoietic drug wherein the reproducibility is a critical part of treatment causing each dose of hematopoietic drug to have the same clinical effect.

Another object is to provide a method of treating the hematopoietic system of ambulatory patients wherein an aerosolized formulation of hematopoietic drug is repeatedly delivered to the patient at the same inspiratory volume (preferably in the range of 0.15 to 0.8 liters) and the same inspiratory flow rate (preferably in the range of 0.1 to 2.0 liters per sec).

Another feature of this invention is that formulations of hematopoietic drug in a highly volatile propellant provide for a fundamentally tamper-resistant package.

It is another object of the invention to provide a metered-dose inhaler canister comprising a formulation of hematopoietic drug packaged in a manner such that it will remain stable and active for long storage times.

A feature of the invention is that it can monitor the amount of aerosolized hematopoietic drug delivered to a patient and record amounts and times of delivery for review by a treating physician.

These and other objects, advantages and features of the present invention will become apparent to those skilled in the art upon reading this disclosure in combination with drawings wherein like numerals refer to like components throughout.

BRIEF DESCRIPTION OF THE DRAWINGS

FIG. 1 is a cross-sectional plan view of a drug delivery device;

FIG. 2 is a cross-sectional plan view of a more preferred embodiment of a drug delivery device;

FIG. 3 is a perspective view showing a pressurized canister with the canister cover components disconnected;

FIG. 4 is a perspective view of another embodiment of the cover components connected and the canister held therein;

FIG. 5 is a graph showing data points plotted in four general areas with the points plotted relative to inspiratory flow rate (on the abscissa) and inspiratory volume (on the ordinate) in two dimensions;

FIG. 6 is a graph showing the four general areas plotted per FIG. 1 now plotted with a third dimension to show the percentage of drug reaching the lungs based on a constant amount of drug released;

FIG. 7 is a three dimensional graph showing the therapeutic values for inspiratory flow rate and inspiratory volume which provide better drug delivery efficiency;

FIG. 8 shows a preferred range of the values shown in FIG. 7;

FIG. 9 shows a particularly preferred range for the values of FIG. 7; and FIG. 10 is a schematic view of an embodiment of a drug delivery device which can be used with the method of the invention; and FIG. 11 is a schematic view of an hematopoietic drug containing package.

DETAILED DESCRIPTION OF THE PREFERRED EMBODIMENTS

Before the present method of hematopoietic system therapy and devices, packages and formulations used in connection with such are described, it is to be understood that this invention is not limited to the particular methodology, devices, packages and formulations described, as such methods, devices, packages and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, reference to "an aerosolized compound" includes a plurality of such compounds, and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

The term "hematopoietic drug" is used herein to describe a drug which has been prepared in a pharmaceutically effective formulation and is useful in hematopoietic system therapy and thus is useful for enhancing the activity of a patient's hematopoietic system. The drug may result in a therapeutically significant increase in red blood cells and/or cause a therapeutically significant increase in early hematopoietic progenitor cells. The term encompasses "EPO" and "erythropoietin" generally and rHuEPO as taught by the '008 patent and/or U.S. Pat. No. 4,667,016 (hereby incorporated by reference) as well as biologically active analogs thereof and cell stem factors (CSF) as disclosed in WO91/05795 also incorporated herein by reference. A hematopoietic drug may be in its native form isolated from mammalian organisms or, alternatively, a product of chemical synthetic procedures or, for example, eucaryotic encoding the erythropoietin amino acid sequences obtained by genomic or cDNA cloning or by gene synthesis. Suitable eucaryotic hosts include yeast (e.g. *S. cerevisiae*) and mammalian (e.g., Chinese hamster ovary (CHO), monkey) cells. Depending upon the host employed, the expression product may be glycosylated with mammalian or other eucaryotic carbohydrates, or it may be non-glycosylated. The present invention contemplates the use of any and all such forms of hematopoietic drugs, including recombinant EPO, especially CHO-derived.

Analogs useful in the practice of this invention include those having one or more amino acid additions, substitutions, and/or deletions as compared to either naturally-derived or recombinant proteins, e.g., rHuEPO. One particular embodiment of an analog comprising an additional amino acid is where an initial methionine amino acid residue is present at amino acid position −1. Substitution analogs may be particularly useful in that such analogs may enable greater and/or differential carbohydrate modifications as compared to either naturally-derived or recombinant proteins, e.g., rHuEPO.

Other useful analogs include those having differential carbohydrate modifications, including molecules containing different patterns of glycosylation, such as the addition or deletion of one or more oligosaccharide chains, differing levels of sialation, etc. See generally *Protein Glycosylation: Cellular, Biotechnical, and Analytical Aspects* (1991), edited by H.S. Conradt, VCH, N.Y., N.Y.

Additionally, other analogs may also be generated. These include analogs wherein the protein is conjugated to another chemical substance, such as polyethylene glycol (PEG). For details, see U.S. Pat. No. 4,179,337, hereby incorporated by reference. Other useful chemical conjugations may include methylation, amidation, etc. Further, one protein (or a biologically active fragment thereof) may be conjugated to another protein molecule. For example, such conjugation may be accomplished by chemical or peptide linkers. See generally *Chemical Reagents for Protein Modification*, 2d. Ed. (1991) R. L. Lundblad, CRC, Boca Raton, Fla., pp. 287–304. Thus, the term hematopoietic drug also refers to chimeric protein molecules, wherein all or a portion of the primary amino acid sequence is combined with a part or all of the primary amino acid sequence of one or more other polypeptide in a contiguous polypeptide chain. For a discussion on the generation of chimetic protein molecules, see *Chemical Reagents for Protein modification*, supra, hereby incorporated by reference. Either by conjugation or by generation of a chimera the following proteins may be linked: G-CSF, GM-CSF, M-CSF, SCF, P-DGF, EPO members of the interleukin family, and members of the FGF family.

As indicated above the term "hematopoietic drug" also encompasses "cell stem factors" or (CSF) which refers to naturally-occurring SCF (e.g., natural human SCF) as well as non-naturally occurring (i.e., different from naturally occurring) polypeptides having amino acid sequences and glycosylation sufficiently duplicative of that of naturally-occurring stem cell factor to allow possession of a hematopoietic biological activity of naturally-occurring stem cell factor. Stem cell factor has the ability to stimulate growth of early hematopoietic progenitors which are capable of maturing to erythroid., megakaryocyte, granulocyte, lymphocyte, and macrophage cells. SCF treatment of mammals results in absolute increases in hematopoietic cells of both myeloid and lymphoid lineages. One of the hallmark characteristics of stem cells is their ability to differentiate into both myeloid and lymphoid cells (Weissman, *Science*, 241, 58–62 (1988)). Treatment of Steel mice with recombinant rat SCF results in increases of granulocytes, monocytes, erythrocytes, lymphocytes, and platelets. Treatment of normal primates with recombinant human SCF results in increases in myeloid and lymphoid cells.

The term "dosing event" shall be interpreted to mean the administration of hematopoietic drug to a patient in need thereof by the intrapulmonary route of administration which event may encompass one or more releases of drug formulation from a drug dispensing device over a period of time of 15 minutes or less, preferably 10 minutes or less, and more preferably 5 minutes or less, during which period multiple inhalations are made by the patient and multiple doses of hematopoietic drug are released and inhaled. Doses of hematopoietic drugs such as erythropoietin (sold as Epogen by Amgen) are measured in units. Sterile solutions containing 2,000, 3,000, 4,000 or 10,000 units in a 1 ml container are available commercially. Dosing is generally begun by the administration of 50 to 100 units/kg of body weight three times a week. Thus, an 80 kg person would receive 4,000 to 8,000 units three times a week. A liquid formulation containing 2.5 to 1,000 $\mu$l more preferably 25 to 100 $\mu$l can be delivered using devices described herein. By adjusting the concentration and types of hematopoietic drug the correct dosage can be administered. As described below it is possible to use hematopoietic drugs which are substantially more potent than erythropoietin and to use synergistic combinations of hematopoietic drugs. By using such, very dilute solutions can be used and it is still possible to give a patient a sufficient dose by the interpulmonary route.

The term "velocity of the drug" shall mean the average speed of particles moving from a drug release point such as a valve to a patient's mouth.

The term "measuring" describes an event whereby both the inspiratory flow rate and inspiratory volume of the patient is determined, measured and/or calculated in order to determine an optimal point in the inspiratory cycle at which to release aerosolized peptide drug formulation. It is also preferable to continue measuring inspiratory flow during and after any drug delivery and to record inspiratory flow rate and volume before, during and after the release of drug. Such reading makes it possible to determine if hematopoietic drug formulation was properly delivered to the patient. A microprocessor or other device can calculate volume based on a measured flow rate. When either flow rate or volume becomes known in any manner it can be said to have been determined.

The term "monitoring" event shall mean measuring lung functions such as inspiratory flow rate, and/or inspiratory volume so that a patient's lung function as defined herein, can be evaluated before and/or after drug delivery thereby making it possible to evaluate the effect, if any, of drug delivery on the patient's lung function.

The term "inspiratory flow rate" shall mean a value of air flow measured, calculated and/or determined based on the speed of the air passing a given point in a measuring device assuming atmospheric pressure ±5% and a temperature in the range of about 10° C. to 40° C.

The term "inspiratory flow" shall be interpreted to mean a value of air flow calculated based on the speed of the air passing a given point along with the volume of the air that has passed that point with the volume calculation being based on integration of the flow rate data and assuming atmospheric pressure, ±5% and temperature in the range of about 10° C. to about 40° C.

The term "inspiratory volume" shall mean a measured, calculated and/or determined volume of air passing a given point into the lungs of a patient assuming atmospheric pressure ±5% and a temperature in the range of 10° C. to 40° C.

The term "inspiratory flow profile" shall be interpreted to mean data calculated in one or more events measuring inspiratory flow and cumulative volume, which profile can be used to determine a point within a patient's inspiratory cycle which is optimal for the release of drug to be delivered to a patient. The point within the inspiratory cycle where drug is released may be based on a point within the inspiratory cycle likely to result in the maximum delivery of drug and based and/or on a point in the cycle most likely to result in the delivery of a reproducible amount of drug to the patient at each release of drug. Repeatability of the amount delivered is the primary criterion and maximizing the amount delivered is an important but secondary criterion. Thus, a large number of different drug release points might be selected and provide for repeatability in dosing provided the selected point is again selected for subsequent releases. To insure maximum drug delivery the point is selected within given parameters.

The term "therapeutic index" refers to the therapeutic index of a drug defined as $LD_{50}/ED_{50}$. The $LD_{50}$ (lethal dose, 50%) is defined as the dose of a drug which kills 50% of the tested animals, and the $ED_{50}$ is defined as the effective dose of the drug for 50% of the individuals treated. Drugs with a therapeutic index near unity (i.e. $LD_{50}/ED_{50}$ is approximately equal to 1) achieve their therapeutic effect at doses very close to the toxic level and as such have a narrow therapeutic window, i.e. a narrow dose range over which they may be administered. Potent hematopoietic drugs may have a narrow therapeutic index thus emphasizing the importance of repeatability in dosing.

The term "therapeutically effective amount" shall mean an amount of hematopoietic drug (as defined herein) which when delivered to the circulatory systems of the patient enhances the activity of the patients hematopoietic system in a measurable and medically meaningful manner and preferably results in red blood cell levels in excess of about 1,000 erythrocytes or more per $\mu$l of blood, more preferably 5–6,000 red blood cells per μl of blood. A therapeutically effective amount will provide a therapeutic effect for a given condition and administration regimen. Dosing of hematopoietic drugs is measured in units and a drug such as EPO is initially administered in amounts of about 50 to 100 units/Kg of body weight. When delivery is made from a aerosolization system with an effective delivery of 20% the dose released would be increased five fold to 250–500 units/kg. Doses can range from 500 units to 100,000 units but are more generally in the range of 20,000 to 40,000 units three times a week to an 80 kg person from a device with a delivery efficiency of about 20%. Adjustments are made in the size of the dose as the other parameters change, i.e., changes in the size of the person and the efficiency of delivery. Further information on what constitutes a therapeutically effective amount is provided above in the description of "dosing event."

The term "SCF" or "stem cell factor" is intended to encompass purified and isolated naturally-occurring SCF (i.e., purified from nature or manufactured such that the primary, secondary and tertiary conformation, and the glycosylation pattern are identical to naturally-occurring material) as well as non-naturally occurring polypeptides having a primary structural conformation (i.e., continuous sequence of amino acid residues) and glycosylation sufficiently duplicative of that of naturally occurring stem cell factor to allow possession of a hematopoietic biological activity of naturally occurring SCF. Such polypeptides include derivatives and analogs.

The terms "formulation" and "liquid formulation" and the like are used interchangeably herein to describe any pharmaceutically active drug by itself or with a pharmaceutically acceptable carrier in flowable liquid form. Such formulations are preferably solutions, e.g. aqueous solutions, ethanoic solutions, aqueous/ethanoic solutions, saline solutions and colloidal suspensions. Formulations can be solutions or suspensions of drug in a low boiling point propellant. Preferred formulations do not include a propellant but do include a liquid carrier and are aerosolized when moved through a porous membrane having pores with a diameter of about 0.5 micron to 6.0 microns. A preferred formulation is a sterile solution of hematopoietic drug (e.g., Epogen) in water, without any preservative and buffered to pH 6.9 ±0.3.

The terms "lung function" and "pulmonary function" are used interchangeably and shall be interpreted to mean physically measurable operations of a lung including but not limited to (1) inspiratory and (2) expiratory flow rates as well as (3) lung volume. Methods of quantitatively determining pulmonary function are used to measure lung function. Methods of measuring pulmonary function most commonly employed in clinical practice involve timed measurement of inspiratory and expiratory maneuvers to measure specific parameters. For example, forced vital capacity (FVC) measures the total volume in liters exhaled by a patient forcefully from a deep initial inspiration. This parameter, when evaluated in conjunction with the forced expired volume in one second ($FEV_1$), allows bronchoconstriction to be quantitatively evaluated. A problem with forced vital capacity determination is that the forced vital capacity maneuver (i.e. forced exhalation from maximum inspiration to maximum expiration) is largely technique dependent. In other words, a given patient may produce different FVC values during a sequence of consecutive FVC maneuvers. The FEF 25–75 or forced expiratory flow determined over the mid-portion of a forced exhalation maneuver tends to be less technique dependent than the FVC. Similarly, the $FEV_1$ tends to be less technique dependent than FVC. In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest air flow rate in liters per minute during a forced maximal exhalation, is well correlated with overall pulmonary function in a patient with asthma and other respiratory diseases. The present invention carries out treatment by administering drug in a drug delivery event and monitoring lung function in a monitoring event. A series of such events may be carried out and repeated over time to determine if lung function is effected or if the efficiency or repeatability or dosing is effected.

Each of the parameters discussed above is measured during quantitative spirometry. A patient's individual performance can be compared against his personal best data, individual indices can be compared with each other for an individual patient (e.g. $FEV_1$ divided by FVC, producing a dimensionless index useful in assessing the severity of acute asthma symptoms), or each of these indices can be compared against an expected value. Expected values for indices derived from quantitative spirometry are calculated as a function of the patient's sex, height, weight and age. For instance, standards exist for the calculation of expected indices and these are frequently reported along with the actual parameters derived for an individual patient during a monitoring event such as a quantitative spirometry test.

General Methodology

A non-invasive means of (1) therapy is provided in a manner which makes it possible to maintain tight control over the amount of drug administered to a patient (2) improve the efficiency of the delivery, and (3) obtain precise timing in terms of when the drug is administered. All three features are obtained by a device which is not directly actuated by the patient, i.e., no button is pushed nor valve released by the patient applying physical pressure. Aerosolized hematopoietic drug is released automatically upon receipt of a signal from a microprocessor programmed to send a signal when data is received (on inspiratory flow and volume) from a monitoring device such as an airflow rate monitoring device.

Delivery devices used to carry out the present invention record specific information relating to both monitoring events and dosing events and can be programmed to react to various changes in order to optimize patient treatment. Specifically, the device includes an ability to record monitoring events in order to develop an inspiratory flow profile of the patient which makes it possible to provide for greater repeatability and efficiency with respect to dosing. Further, the device specifically records the time and amount of hematopoietic drug released at each dosing event. The day and time of day of drug release is recorded.

The device is equipped with a visual and audio signaling means which tell the patient when and/or how much peptide drug to take. The audio means is programmed so as to send an audio signal when the patient is to begin a monitoring event to be followed by a dosing event. The visual display indicates specific information such as providing instructions to the patient including "conduct monitoring event" and "proceed with dosing event." Further, the visual display will indicate a calendar of days and specifically indicate on the calendar when dosing took place on the given day. Accordingly, the patient can quickly determine by visual examination whether hematopoietic drug was delivered on any given day. It is often important to administer such drugs at the same time each day as natural hormone release (and thus hormone administration) is closely connected to the chronobiology of the patient. Drugs such as EPO are hormones.

A patient using the device withdraws air from a mouthpiece and the inspiratory rate, and calculated inspiratory volume of the patient are measured one or more times in a monitoring event which determines a preferred point in an inhalation cycle for the release of a dose of peptide drug. Inspiratory flow is measured and recorded in one or more monitoring events for a given patient in order to develop an inspiratory flow profile for the patient. The recorded information is analyzed by the microprocessor in order to deduce a preferred point within the patient's inspiratory cycle for the release of hematopoietic drug with the preferred point being calculated based on the most likely point to result in (1) a reproducible delivery event and (2) efficiency of drug delivery i.e., a high percentage of released aerosolized drug get into the circulatory system of the patient.

The device can be (and in one preferred embodiment is) present so that it will release drug within specific parameters as per FIGS. 7, 8 and 9. The device will measure and release drug in a single breath, i.e., there is no need for monitoring events or breath measurement reading of any kind prior to the breath during which drug is released.

The device of the present invention can be used to, and actually does, improve the efficiency of drug delivery. The improved efficiency is what makes it possible to carry out this therapy with a hand-held device. However, without reproducibility the method would not be practical. The device provides the reproducibility of the release of a tightly controlled amount of drug at a particular point in the respiratory cycle. This insures the delivery of a controlled and repeatable amount of drug to the lungs of each individual patient.

The combination of automatic control of the release, combined with frequent monitoring events (or a preset range as per FIGS. 7, 8 and 9) in order to calculate the optimal flow rate and time for the release of peptide drug, combine to provide a repeatable means of delivering hematopoietic drug to a patient. Because the drug is released automatically and not manually, it can be predictably and repeatedly release the same amount each time or release the amount desired at that particular dosing event. Because drug release points are set within specific ranges as per FIGS. 7, 8 and 9 and release is made based on an actual measurement, the amount of drug released and/or the point in the inspiratory cycle of the release can be readjusted based on the particular condition of the patient. For example, if the patient is suffering from a condition which allows for a certain degree of pulmonary insufficiency, such may be taken into account by the microprocessor which may readjust the point of release of the hematopoietic drug in a manner calculated to provide for the administration of the same amount of drug to the patient at each dosing event.

Repeatability as per Figures

FIG. 5 is a two-dimensional graph wherein the inspiratory flow rate is plotted against the inspiratory volume. The patient's inspiratory flow rate and inspiratory volume are simultaneously and separately measured. This measurement may be made before or during the same inhaled breath that the drug is released. The measurement is taken and the information obtained from the measurement provided to a microprocessor which microprocessor is programmed to release drug (1) at the same point relative to inspiratory flow and inspiratory volume at each release of drug and (2) to select that point within prescribed parameters of inspiratory flow rates and inspiratory volumes. In the particular results plotted in FIG. 5 the microprocessor was programmed to release drug in four general areas with respect to the inspiratory flow rate and inspiratory volume parameters. This resulted in data points being plotted in four general areas on the two-dimensional graph of FIG. 5. The four areas are labeled 1, 2, 3 and 4. In area 1 (showing solid triangles), the drug was released when the patient's inspiratory flow rate was "slow to medium" (0.10 to 2.0 liters per sec) with an "early" inspiratory volume of 0.15 to 0.8 liters. In area 2 (showing open triangles), the drug was released at a "slow" inspiratory rate/0.10 to 1.0 liters/sec) and a "late" volume (1.6 to 2.8 liters). In area 3 (showing solid diamonds), the drug was released at a "fast" inspiratory flow rate (3.5 to 4.5 liters/sec) and a "late" volume. In area 4 (showing solid circles), the drug was released at a "fast" inspiratory flow rate and an "early" inspiratory volume.

The results shown in FIG. 5 were obtained while administering a radioactively labeled drug to a human. After the administration of the drug it was possible to determine not only the amount of drug, but the pattern of drug deposited within the lungs of the patient. Using this information two conclusions were reached. Firstly, it was determined that it is important to simultaneously and separately consider (in real time) both inspiratory flow rate and inspiratory volume when determining the point for drug release for intrapulmonary drug delivery. Changes in either parameter can greatly effect the amount of drug deposited. Thus, when treating a patient the drug should be released at approximately (±10%, preferably ±5% and most preferable as close as possible to the first release point) the same inspiratory flow rate and inspiratory volume each time—going back to the same point each time for the same patient ensures repeatable dosing. In practice the tighter the point is defined the greater the repeatability of dosing. However, if the point is defined too precisely it can be difficult for the patient to obtain that rate/volume point again. Thus, some degree of tolerance is generally applied. Secondly, it was found that within particular ranges with respect to inspiratory flow rate and inspiratory volume it was possible to obtain a consistently high percentage amount of drug deposited in the lung. Such results are shown graphically within the three dimensional graph as shown in FIG. 6.

Efficiency as per Figures

The third dimension as shown in FIG. 6 (the height of the four columns) indicates the percentage amount of drug deposited based on the total amount of drug released to the patient. The area labeled 1 clearly showed the highest percentage of drug delivered to the patient based on the amount of drug released. Using this information it was possible to calculate a specific area regarding inspiratory flow rate and inspiratory volume at which it is possible to obtain not only a high degree of repeatability in dosing, but obtain a higher percentage of drug being delivered based on the percentage of drug released. Specifically, it was determined that the drug should be released within an inspiratory flow rate range of 0.10 to 2.0 liters per second and at an inspiratory volume in the range of about 0.15 to about 0.80 liters. This range is shown by the rectangularly shaped column of FIG. 7.

Efficiency By Drug Potency

Efficiency of treatment can be significantly improved by the administration of a more potent hematopoietic drug. Drugs such as SCF can have a much greater therapeutic effect on the hematopoietic system than drugs such as EPO. The SCF is preferably characterized by being the product of procaryotic or eucaryotic host expression (e.g., by bacterial, yeast, higher plant, insect and mammalian cells in culture) of exogenous DNA sequences obtained by genomic or CDNA cloning or bu gene synthesis. That is, in a preferred embodiment, SCF is "recombinant SCF." The products of expression in typical yeast (e.g., *Saccharomyces cerevisiae*) or procaryote (e.g., *E. coli*) host cells are free of association with any mammalian proteins. The products of expression in vertebrate {e.g., non-human mammalian (e.g., COS or CHO) and avian} cells are free of association with any human proteins. Depending upon the host employed hematopoietic drugs of the invention may be glycosylated with mammalian or other eucaryotic carbohydrates or may be non-glycosylated. The host cell can be altered using techniques such as those described in Lee, et al., Biol. Chem. 264, 13848 (1989) hereby incorporated by reference. Hematopoietic drugs used in the invention may also include an initial methionine amino acid residue (at position −1).

In addition to naturally-occurring allelic forms of SCF, it is possible to use other SCF products such as polypeptide analogs of SCF. Such analogs include fragments of SCF. Following the procedures of (Alton, et al., WO 83/04053 incorporated herein by reference), one can readily design and manufacture genes coding for microbial expression of polypeptides having primary conformations which differ from that herein specified for in terms of the identify or location of one or more residues (e.g., substitutions, terminal and intermediate additions and deletions). Alternately, modifications of cDNA and genomic genes can readily accomplished by well-known site-directed mutagenesis techniques and employed to generate analogs and derivatives of SCF. Such products share at least one of the biological properties of SCF but may differ in others. As examples, potent hematopoietic drug used with the invention include those which are shortened by e.g., deletions; or those which are more stable to hydrolysis (and, therefore, may have more pronounced or longer-lasting effects than naturally-occurring version); or which have been altered to delete or to add one or more potential sites for O-glycosylation and/or N-glycosylation or which have one or more cysteine residues deleted or replaced by, e.g., alanine or serine residues and are potentially more easily isolated in active form from microbial systems; or which have one or more tyrosine residues replaced by phenylalanine and bind more or less readily to target protein or to receptors on target cells. Also comprehended are polypeptide fragments duplicating only a part of the continuous amino acid sequence or secondary conformations within SCF, which fragments may possess one property of SCF (e.g., receptor binding) and not others (e.g., early hematopoietic cell growth activity). Competitive antagonists may be quite useful in, for example, cases of overproduction of SCF or cases of human leukemias where the malignant cells overexpress receptors for SCF, as indicated by the overexpression of SCF receptors in leukemic blasts.

The potency of SCF drugs alone and in certain synergistic combinations can be substantially greater than the potency of EPO alone. Although any of the hematopoietic drugs can be prepared in concentration of from 0.5% to 50% the formulations are generally very dilute, e.g., 1% to 5% of drug in a solution of water and other excipients such as buffers. One to five mg of hematopoietic drug could be dissolved in 1 cc of water to provide a 1–5% solution. A dose of 100 μl of such a solution would include 1,000 units to 5,000 units of drugs if the drug included 10,000 units/mg and would include 10,000 units to 50,000 units if the drug was 10 times that potent.

Obtaining Repeatable Dosing

In that intrapulmonary drug delivery systems often provide for erratic dosing it is important to provide a method which allows for consistent, repeatable dosing. This is obtained by simultaneously and separately considering both inspiratory flow rate and inspiratory volume in order to determine a point by its abscissa and ordinate. If both measurements are separately considered the drug can be released anywhere along the abscissa and ordinate scales shown in FIG. 5. Once a point is selected (such as by randomly selecting a point in box 1 of the graph of FIG. 5) that selected point (with the same coordinates) is used again and again by a given patient to obtain repeatable dosing. If only one parameter is measured (abscissa or ordinate) and drug is released based on that parameter the drug release point is defined by a line on the graph of FIG. 5. When drug is released again the release can be at any point on that line. For example, the inspiratory flow rate (measured horizontally on the abscissa) might be defined by a point. However, the inspiratory volume (which was not measured and/or considered) would be defined only by a vertical line. Thus, subsequent releases would be at different volumes along that vertical line and the dosing would not be consistent. By measuring both inspiratory flow rate on the abscissa and inspiratory volume on the ordinant the coordinates will mark a point for drug release. That point can be found again and again to obtain repeatability in dosing. The same point should be selected each time as closely as possible and within a margin of errors of ±10% with respect to each criteria. The margin for error can be increased and still maintain acceptable levels of repeatable dosing—but the error should keep the drug release point inside the box 1 of FIG. 5.

Obtaining Efficient Dosing

Figure 5:
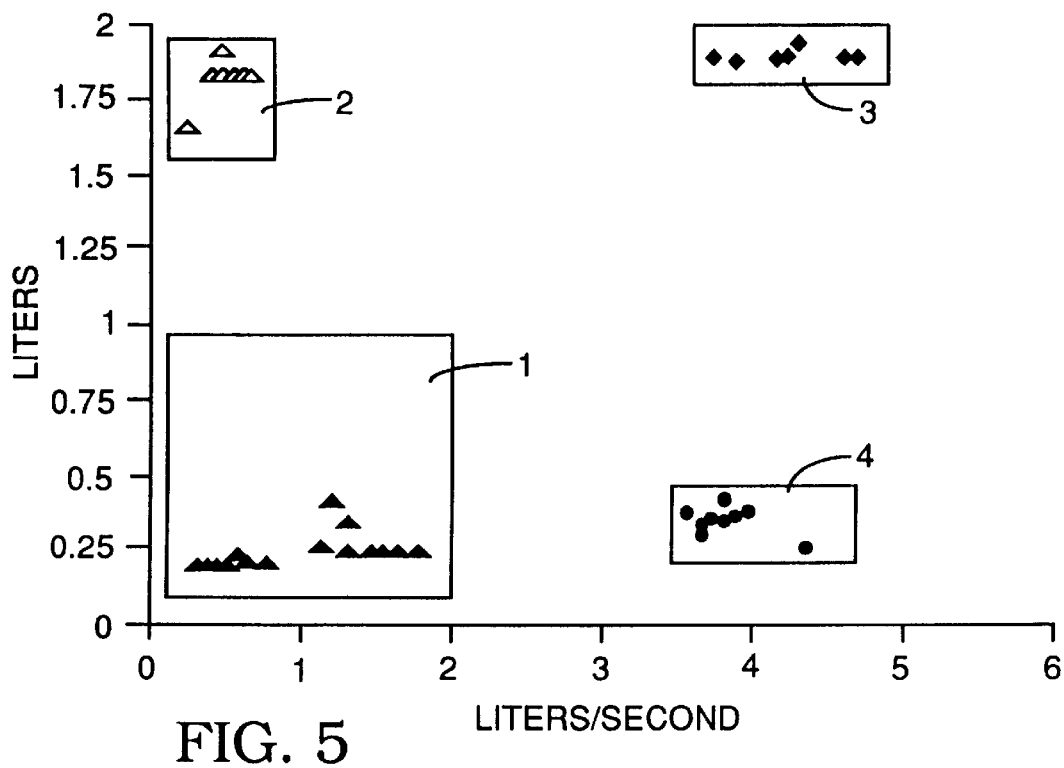
Figure 6:
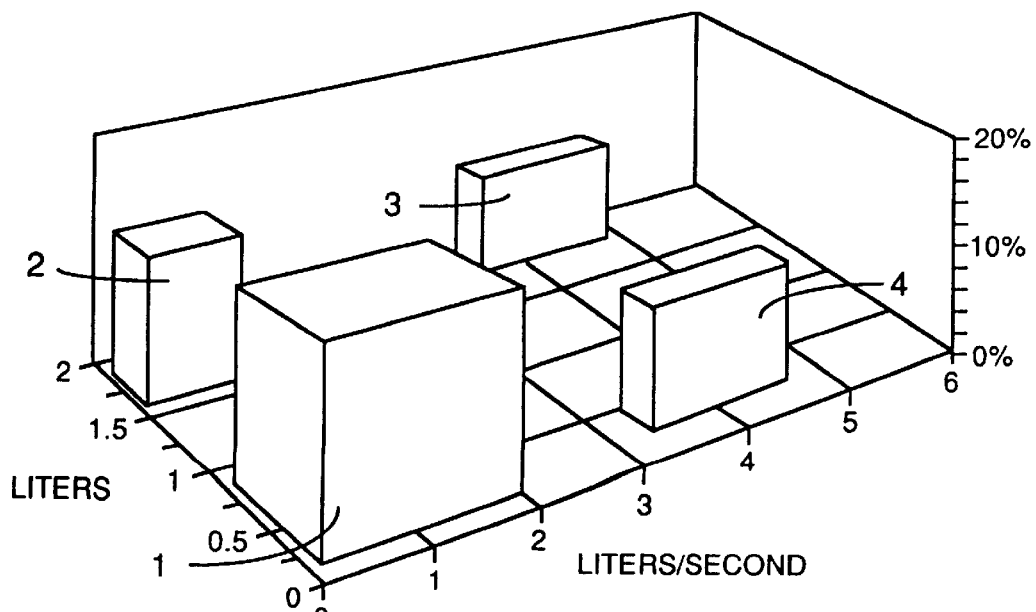
Figure 7:
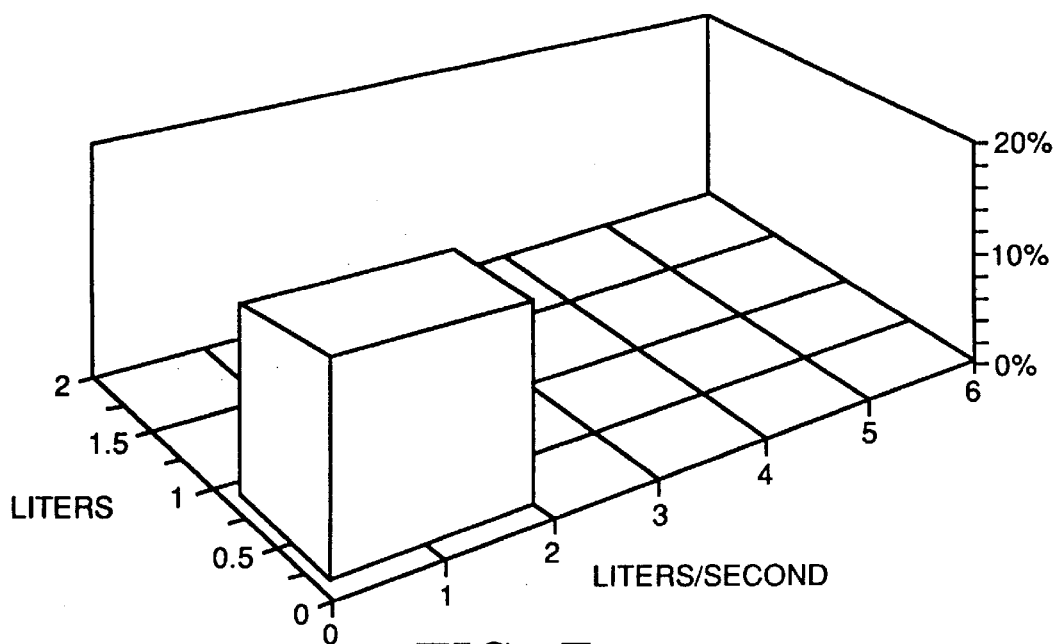

By examining delivery of drug associated with the data points plotted in FIG. 5, it is possible to determine a preferred and particularly preferred and most preferred range (as per FIGS. 7, 8 and 9) which allow for increased efficiency in the delivery. The preferred range of FIG. 7 shows drug released at a volume of 0.15 to 0.8 liters and rate of 0.10 to 2.0 liters/second. The particularly preferred range plotted in FIG. 8 indicates that the inspiratory flow should be within the range of 0.2 to about 1.8 liters per second with an inspiratory volume in the range of 0.15 to about 0.4 liters. The most preferred range (FIG. 9) is from about 0.15 to about 1.8 liters per second for the inspiratory flow rate and about 0.15 to about 0.25 liters for the inspiratory volume.

Figure 8:
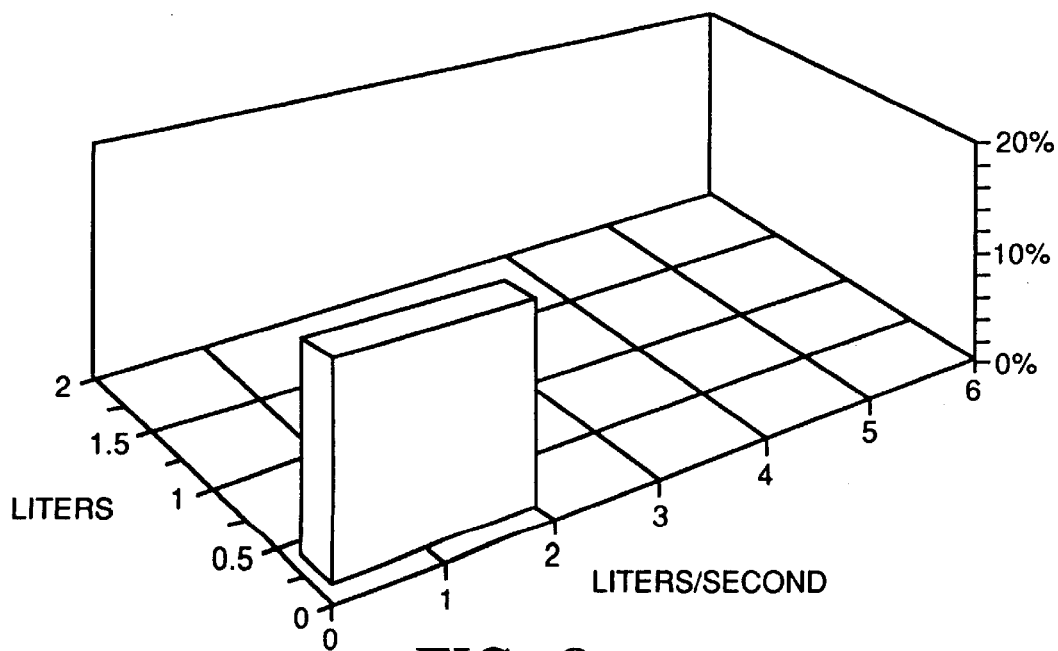
Figure 9:
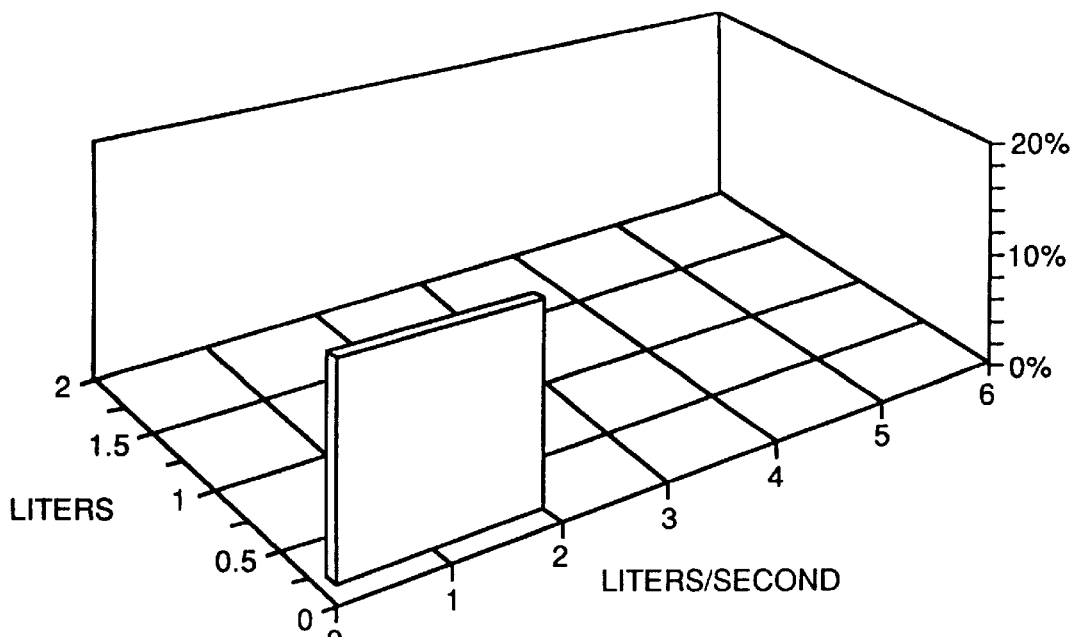

Based on the above it will be understood that effective treatment of the hematopoietic system can be obtained by (1) repeatedly delivering aerosolized formulation to a patient at the same simultaneously and separately measured inspiratory flow rate and inspiratory volume and (2) releasing drug to the patient within specified therapeutically effective ranges as shown within FIGS. 7, 8 and 9. The invention involves releasing drug (after measuring) inside the ranges as per FIGS. 7, 8 or 9. Thus, the release could begin inside or outside the range. Preferably the drug release begins inside the range and more preferable begins and ends inside the ranges of FIGS. 7, 8 or 9.

Efficiency by Synergistic Drug Combinations

The potency of hematopoietic drug can be improved by providing different combinations of drugs. Stem cell factor may be combined with each other and with one or more drugs selected from the group consisting of: EPO, G-CSF, GM-CSF, CSF-1, IL-1, IL-2, IL-3, IL-4, IL-5, IL-6, IL-7, IL-8, IL-9, IL-10, IL-11, IL-12, IGF-1, or LIF (Leukemic Inhibitory Factor.

The synthetic effect obtained by some combination is shown below:

Recombinant Human SCF Synergy With Other Human Colony Stimulating Factors

|  | Colony #/10$^5$ cells (14 Days) |
| --- | --- |
| mock | 0 |
| hG-CSF | 32 ± 3 |
| hG-CSF + hSCF | 74 ± 1 |
| hGM-CSF | 14 ± 2 |
| hGM-CSF + hSCF | 108 ± 5 |
| hIL-3 | 23 ± 1 |
| hIL-3 + hSCF | 108 ± 3 |
| hEPO | 10 ± 5 |
| hEPO + IL-3 | 17 ± 1 |
| hEPO + hSCF | 86 ± 10 |
| hSCF | 0 |

Based on the data shown above it can be seen that particular synergistic combinations such as hGM–CSF+ hSCF and hIL–3+hSCF have a potency which is more than 10 fold greater than that of hEPO.

Hand-Held Drug Delivery Device

The methodology of the invention may be carried out using a portable, hand-held, battery-powered device as per U.S. Pat. No. 5,394,866, issued Mar. 7, 1995 incorporated herein by reference. In accordance with a more preferred embodiment the methodology of the invention could be carried out using the device, dosage units and system disclosed in U.S. patent application Ser. No. 08/247,012 filed May 20, 1994. In accordance with this system the hematopoietic drug is included in an aqueous formulation which is aerosolized by moving the formulation through a porous membrane which includes pores having a diameter in the range off about 0.5 to about 6.0 microns. Alternatively, the methodology of the invention could be carried out using a mechanical (non-electronic) device. Those skilled in the art will recognize that various components can be mechanically set to actuate at a given inspiratory flow rate (e.g. a spring biased valve) and at a given volume (e.g. a spinable flywheel which rotates a given amount per a given volume). The components of such devices could be set to allow drug release inside the parameters as per the attached figures.

The drug which is released to the patient may be in a variety of different forms. For example, the drug may be an aqueous solution of drug, i.e., drug dissolved in water and formed into small particles to create an aerosol which is delivered to the patient. Alternatively, the drug may be in a solution wherein a low-boiling point propellant is used as a solvent.

Some hematopoietic drugs are subject to being degraded more quickly when in solution such as an aqueous solution. Preferably such drug are packaged in a dry form and mixed with water prior to administration. Alternately, the drug is kept in the form of a dry powder which is intermixed with an airflow in order to provide for particlized delivery of drug to the patient.

Regardless of the type of hematopoietic drug or the form of the drug formulation, it is preferable to create drug particles having a size in the range of about 1.0 to 12 microns. By creating drug particles which have a relatively narrow range of size, it is possible to further increase the efficiency of the drug delivery system and improve the repeatability of the dosing. Thus, it is preferable that the particles not only have a size in the range of 1.0 to 12 microns but that the mean particle size be within a narrow range so that 80% or more of the particles being delivered to a patient have a particle diameter which is within ±50% of the average particle size, preferably ±20% and more preferably ±5% of the average particle size.

The velocity at which the aerosolized drug is released to the patient is also important in terms of obtaining a high degree of repeatability in dosing and providing for a high percentage of drug being delivered to the patient's lungs. Most preferably, the drug is released from a container in a direction which is normal to the patient's airflow. After being released the particles are moved along with the patient's airflow at the same speed as the air flow. The drug may be released directly upward so that its flow is at a 90° angle with respect to the patient's inspiratory flow which is directly horizontal. After being released, the drug velocity decreases and the drug particles remain suspended for a sufficient period of time to allow the patient's inspiration to draw the drug into the patient's lungs.

The drug is preferably released in a aerosolized burst having been moved through a porous membrane with pores 0.5 to 6.0 microns in diameter. However, the drug may be released from a pressurized canister which includes a propellant. It is preferable to release the drug so that its velocity in the direction from the drug release point to the patient matches the patient's inspiratory flow rate. Preferably the velocity at the time of release is slower than the patient's inspiratory flow rate and is most preferably about zero and then increases to match the speed of the patient's inspiratory flow. The velocity may be slightly negative, i.e., in a direction away from the patient. The velocity may range from −2.0 liters/sec to 2.0 liters/sec and is preferably zero at the time of release. It is not desirable to project the drug toward the patient at a rate above the speed of the patient's breath as such may result in drug being deposited on the back of the patient's throat. Thus, the drug release speed should be equal to or less than the breath speed. The actual speed of release can vary depending on factors such as the particle size, the particle composition and the distance between the point of release and the patient. The velocity is preferably such that the particles will (due to air resistance) slow to zero velocity after traveling a distance of about 2 centimeters or less (i.e., the particles slow in speed so as to match the speed of the patient's breath and are thus carried along with the patient's inspiratory flow). In general, the shorter the distance required to slow the particles to zero velocity the better.

An aerosol may be created by forcing drug through pores of a membrane which pores have a size in the range of about 0.5 to 6.0 microns. When the pores have this size the particles which escape through the pores to create the aerosol will have a diameter in the range of 1.0 to 12 microns. Drug particles may be released with an air flow intended to keep the particles within this size range. The creation of small particles may be facilitated by the use of the vibration device which provides a vibration frequency in the range of about 800 to about 4000 kilohertz. Those skilled in the art will recognize that some adjustments can be made in the parameters such as the size of the pores from which drug is released, vibration frequency, pressure, and other parameters based on the density and viscosity of the formulation keeping in mind that the object is to provide aerosolized particles having a diameter in the range of about 1.0 to 12 microns.

The drug formulation may be a low viscosity liquid formulation. The viscosity of the drug by itself or in combination with a carrier must be sufficiently low so that the formulation can be forced out of openings to form an aerosol, e.g., using 20 to 200 psi to form an aerosol preferably having a particle size in the range of about 1.0 to 12 microns.

Drug may be stored in and/or released from a container of any desired size. In most cases the size of the container is not directly related to the amount of drug being delivered in that most formulations include relatively large amounts of excipient material e.g. water or a saline solution. Accordingly, a given size container could include a wide range of different doses by varying drug concentration.

The dose or amount of hematopoietic drug delivered to the patient will vary greatly depending on the particular drug being delivered. In accordance with the present invention it is possible to deliver a wide range of hematopoietic drugs. For example, drugs included within the container could be erythropoietin as defined in U.S. Pat. No. 5,354,934, granulocyte colony stimulating factor as per WO/20069, any stem cell factor as per WO/91/05795, all of which publications are incorporated herein by reference to disclose and describe hematopoietic drugs.

Drug containers may include indices which may be electronic and may be connected to a power source such as a battery. When the indices are in the form of visually perceivable numbers, letters or any type of symbol capable of conveying information to the patient. Alternatively, the indices may be connected to a power source such as a battery when the indices are in the form of magnetically, optically or electronically recorded information which can be read by a drug dispensing device which in turn provides visual or audio information to the user. The indices can be designed for any desired purpose but in general provides specific information relating to the day and/or time which the drug within a container should be administered to the patient. Such indices may record, store and transfer information to a drug dispensing device regarding the number of doses remaining in the container. The containers may include labeling which can be in any format and could include days of the month or other symbols or numbers in any variation or language.

In addition to disclosing specific information regarding the day and time for drug delivery the indices could provide more detailed information such as the amount of drug dispensed from each container which might be particularly useful if the containers included different amounts of drug. Further, magnetic, optical and/or electronic indices could have new information recorded onto them which information could be placed there by the drug dispensing device. For example, a magnetic recording means could receive information from the drug dispensing device indicating the precise time which the drug was actually administered to the patient. In addition to recording the time of delivery the device could monitor the expected efficacy of the delivery based on factors such as the inspiratory flow rate which occurred following the initial release of drug. The information recorded could then be read by a separate device, interpreted by the care-giver and used to determine the usefulness of the present treatment methodology. For example, if the patient did not appear to be responding well but the recorded information indicating that the patient had taken the drug at the wrong time or that the patient had misdelivered drug by changing inspiratory flow rate after initial release it might be determined that further education in patient use of the device was needed but that the present dosing methodology might well be useful. However, if the recordings indicated that the patient had delivered the drug using the proper techniques and still not obtained the correct results a different drug or dosing methodology might be recommended.

The method of hematopoietic therapy is carried out using a hand-held, portable device comprised of (a) a device for holding a disposable package comprised of at least one but preferably a number of drug containers, (b) a propellant or a mechanical mechanism for moving the contents of a container through a porous membrane (c) a monitor for analyzing the inspiratory flow, rate and volume of a patient, and (d) a switch for automatically releasing or firing the mechanical means after the inspiratory flow and/or volume reaches a threshold level. The device may also include a transport mechanism to move the package from one container to the next. The entire device is self-contained, light weight (less than 1 kg preferably less than 0.5 kg loaded) and portable. The device will release a precise predetermined dose at each release, i.e., it is not a device which continually dispenses drug such as a nebulizer.

The device may include a mouth piece at the end of the flow path, and the patient inhales from the mouth piece which causes an inspiratory flow to be measured within the flow path which path may be in a non-linear flow-pressure relationship. This inspiratory flow causes an air flow transducer to generate a signal. This signal is conveyed to a microprocessor which is able to convert, continuously, the signal from the transducer in the inspiratory flow path to a flow rate in liters per minute. The microprocessor can further integrate this continuous air flow rate signal into a representation of cumulative inspiratory volume. At an appropriate point in the inspiratory cycle, the microprocessor can send a signal to an actuation means (and/or a vibration device below the resonance cavity). When the actuation means is signaled, it causes the mechanical means (by pressure or vibration) to move drug from a container on the package into the inspiratory flow path of the device and ultimately into the patient's lungs. After being released, the drug and carrier will pass through a porous membrane which is vibrated to aerosolize the formulation and thereafter the lungs of the patient. Containers and systems of the type described above are disclosed and described in U.S. patent application Ser. No. 08/247,012 filed May 20, 1994 which is incorporated herein by reference to disclose and describe such containers and systems.

It is important to note that the firing threshold of the device is not based on a single criterion such as the rate of air flow through the device or a specific time after the patient begins inhalation. The firing threshold is based on an analysis of the patient's inspiratory flow profile. This means that the microprocessor controlling the device takes into consideration the instantaneous air flow rate as well as the cumulative inspiratory flow volume. Both are simultaneously considered together in order to determine the optimal point in the patient's inspiratory cycle most preferable in terms of (1) reproducibly delivering the same amount of drug to the patient with each release of drug by releasing drug at the same point each time and (2) maximizing the amount of drug delivered as a percentage of the total amount of drug released by releasing with the parameters described herein.

The device preferably includes a means for recording a characterization of the inspiratory flow profile for the patient which is possible by including a microprocessor in combination with a read/write memory means and a flow measurement transducer. By using such devices, it is possible to change the firing threshold at any time in response to an analysis of the patient's inspiratory flow profile, and it is also possible to record drug dosing events over time. In a particularly preferred embodiment the characterization of the inspiratory flow can be recorded onto a recording means on the disposable package.

The details of a drug delivery device which includes a microprocessor and pressure transducer of the type used in connection with the present invention are described and disclosed within U.S. patent application Ser. No. 07/664,758 filed on Mar. 5, 1991 entitled "Delivery of Aerosol Medications for Inspiration" which application is incorporated in its entirety herein by reference, and it is specifically incorporated in order to describe and disclose the microprocessor and program technology used therewith. (See also U.S. Pat. No. 5,394,866, issued Mar. 7, 1995 also incorporated by reference.)

The use of such a microprocessor with a drug delivery device is disclosed in U.S. Pat. No. 5,392,768, issued Feb. 28, 1995 incorporated herein by reference. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, a microprocessor, containing read only memory which in turn contains the pre-programmed information, is plugged into the device. For each of these three embodiments, changing the programming of the memory device readable by a microprocessor will radically change the behavior of the device by causing the microprocessor to be programmed in a different manner. This is done to accommodate different types of hematopoietic drugs.

In a preferred embodiment of the methodology of the invention several different criteria are considered. (1) The inspiratory flow rate and inspiratory volume are simultaneously and separately considered to insure repeatability. (2) The drug is released inside the parameters of FIGS. 7, 8 or 9 with FIG. 9 parameters being most preferred. (3) The particle size of the released drug is in the range of 1.0 to 12 microns and 80% or more and the particles have the same size as the average particle size ±10% in size. (4) The drug particles are released at a velocity which is obtained at a flow rate (relative to the patient's inspiratory flow) in the range of −2.0 liters/sec. and less than 2.0 liters/sec. As indicated early the actual velocity can vary based on a number of factors. The release velocity should be determined so that the particles are at or are slowed to zero velocity after traveling about 0.5 to 2 cm from the release point. The speed being measured from the drug release point in a direction toward the back of the throat of the patient. A velocity of zero relative to the patient's inspiration means the drug particles move at the same speed as the patient's inspiration.

After dosing a patient with a hematopoietic drug it is desirable to take blood samples and make adjustments as needed to obtain the desired drug to blood ratio. In accordance with all methods the patient does not push a button to release drug. The drug is released automatically by signals from the microprocessor using measurements obtained.

The amount of hematopoietic drug delivered to the patient will vary greatly depending on the particular drug being delivered. In accordance with the present invention it is possible to deliver a wide range of different drugs. The drugs must pass through pulmonary membranes and provide for a therapeutic dose from a hand-held device. Preferred drugs include recombinant EPO and G-CSF in that each are FDA approved and commercially available and human cell stem factor (CSF) as per WO91/05795 due to greater potency. The amount of hematopoietic drug administered is generally measured in units. With drugs such as EPO a 10,000 unit dose can be delivered by the administration of as little as 1 ml of solution. When delivering CSF and synergistic combinations thereof the amount can be reduced 0.1 ml of solution or less or by delivering a 1 ml of solution diluted to a concentration which is 1/10 the concentration of the EPO solution.

These doses are based on the assumption that when intrapulmonary delivery methodology is used the efficiency of the delivery is approximately 20% and adjustments in the amount released must be made in order to take into account the efficiency of the device. The differential between the amount of drug actually released from the device and the amount of drug actually delivered to the patient varies due to a number of factors. As shown in FIGS. 6–9 devices used with the present invention are approximately 20% efficient, however, the efficiency can be as high as 50% or more meaning that as little as 20% of the released peptide hormone drug may actually reach the circulatory system of the patient and as much as 50% or more might be delivered. The efficiency of the delivery will vary somewhat from patient to patient and must be taken into account when programming the device for the release of hematopoietic drug. In general, a conventional metered dose inhaling device is about 10% efficient and a conventional nebulizer is less than 10% efficient.

When administering hematopoietic drug using an inhalation device of the present invention, the entire dosing event can involve the administration of anywhere from 0.01 to 10 ml of solution, but more preferably involves the administration of approximately 25 $\mu$l to 100 $\mu$l of solution of hematopoietic drug. A 100 $\mu$l dose of a 1% solution of a hematopoietic drug containing 100,000 units per mg would contain 100,000 units. If 20% of the dose actually reached the patient's circulatory system the patient would receive a dose equivalent to 20,000 units I.V. The large variation in the amounts which might be delivered are due to the fact that different drugs have greatly different potencies and concentrations in the solutions may be delivered from devices which vary greatly in terms of the efficiency of drug delivered. The entire dosing event may involve several inhalations by the patient with each of the inhalations being provided with multiple bursts of hematopoietic drug from the device.

In addition to drug potency and delivery efficiency, drug sensitivity must be taken into consideration. The present invention makes it possible to vary dosing over time if the sensitivity of the patient changes and/or if user compliance and/or lung efficiency changes over time.

Dynamic Particle Size Adjustment

When aerosolized particles are released from a drug delivery device in accordance with the methodology of the invention, the particles can change in size due to evaporation of water from the particles. Further, if the surrounding atmosphere is particularly humid, the particles can increase in size. In order to obtain reproducibility in dosing, it is desirable to create a surrounding environment such that the particles do not increase or decrease in size regardless of the humidity. In order to obtain such, it is possible to incorporate into the device a means for adding energy to the air surrounding the aerosolized particles. By doing such, it is possible to minimize the effect of water vapor which might be present within the air and to obtain a predetermined amount of evaporation of water from the particles. It is also possible to add water vapor so as to saturate the atmosphere surrounding the particles and thereby prevent the particles from undergoing evaporation. The correct technique to be used depends on the particular drug and the particular situation which the device is being used within. Various means for effecting the size of particles are disclosed within U.S. patent application Ser. No. 08/313,461 filed Sep. 27, 1994, which application is incorporated herein in its entirety and specifically incorporated in order to disclose means for dynamically effecting the size of aerosolized particles.

Dosing Methodology

Based on the above, it will be understood that the dosing or amount of drug actually released from the device can be changed based on the most immediately prior monitoring event wherein the inspiratory flow of a patient's inhalation is measured.

The dosing program can be designed with some flexibility. For example, if the patient normally requires 4,000 units of drug, the microprocessor of the inhalation device can be programmed to prevent further release of drug after 5,000 units have been administered within a given day. Setting a slightly higher limit would allow for the patient to administer additional hematopoietic drug, if needed, due to misdelivery of hematopoietic drug such as due to coughing or sneezing during an attempted delivery.

The ability to prevent overdosing is a characteristic of the device due to the ability of the device to monitor the amount of hematopoietic drug released and calculate the approximate amount of hematopoietic drug delivered to the patient based on monitoring given events. The ability of the present device to prevent overdosing is not merely a monitoring system which prevents further manual actuation of a button. As indicated above, the device used in connection with the present invention is not manually actuated, but is fired (i.e., drug released) in response to an electrical signal received from a microprocessor (which received data from a monitoring device such as a device which monitors inspiratory flow) and allows the actuation of the device upon achieving an optimal point in a inspiratory cycle. When using the present invention, each release of the valve is a release which will administer drug to the patient in that the valve is released in response to patient inhalation. More specifically, the device does not allow for the release of drug merely by the manual actuation of a button to fire a burst of aerosolized drug into the air or a container.

The microprocessor will also include a timing device. The timing device can be electrically connected with visual display signals as well as audio alarm signals. Using the timing device, the microprocessor can be programmed so as to allow for a visual or audio signal to be sent when the patient would be normally expected to administer hematopoietic drug. In addition to indicating the time of administration (preferably by audio signal), the device can indicate the amount of drug which should be administered by providing a visual display. For example, the audio alarm could sound alerting the patient that drug should be administered. At the same time, the visual display could indicate "1,000 units" as the amount of drug to be administered. At this point, a monitoring event could take place. After completion of the monitoring event, administration would proceed and the visual display would continually indicate the remaining amount of drug which should be administered. After the predetermined dose of 1,000 units had been administered, the visual display would indicate that the dosing event had ended. If the patient did not complete the dosing event by administering the stated amount of drug, the patient would be reminded of such by the initiation of another audio signal, followed by a visual display instructing the patient to continue administration.

Additional information regarding dosing of EPO and G-CSF and be found in the PDR, The AMA's "Drug Evaluations Annual 1993" at pages 2229 to 2239 and Harrison's—*Principles of Internal Medicine* (most recent edition of each). Harrison's is published by McGraw Hill Book Company, New York, and all three are incorporated herein by reference to disclose information regarding the dosing of hematopoietic drugs.

Utility

There are many diseases which are treatable with the hematopoietic drug delivery methods of this invention. These include the following: myelofibrosis, myelosclerosis, osteoporosis, metastatic carcinoma, acute leukemia, multiple myeloma, Hodgkin's disease, lymphoma, Gaucher's disease, Niemann-Pick disease, Lettere-Siwe disease, refractory erythroblastic anemia, Di Guglielmo syndrome, congestive splenomegaly, Hodgkin's disease, Kala azar, sarcoidosis, primary splenic pancytopenia, miliary tuberculosis, disseminated fungus disease, Fulminating septicemia, malaria, vitamin $B_{12}$ and folic acid deficiency, pyridoxine deficiency, Diamond Blackfan anemia, hypopigmentation disorders such as piebaldism and vitiligo.

Enhancement of growth in non-hematopoietic stem cells such as primordial germ cells, neural crest derived melanocytes, commissural axons originating from the dorsal spinal cord, crypt cells of the gut, mesonephric and metanephric kidney tubules, and olfactory bulbs is of benefit in states where specific tissue damage has occurred to these sites. SCF is useful for treating neurological damage and is growth factor for nerve cells. SCF is useful during in vitro fertilization procedures or in treatment of infertility states. SCF is useful for treating intestinal damage resulting from irradiation or chemotherapy.

There are stem cell myeloproliferative disorders such ass polycythemia vera, chronic myelogenous leukemia, myeloid metaplasia, primary thrombocythemia, and acute leukemias which ar treatable with SCF, anti-SCF antibodies, or SCF-toxin conjugates.

There are numerous cases which document the increases proliferation of leukemic cells to the hematopoietic cell growth factors G-CSF, GM-CSF, and IL-3 [Delwell, et ala., *Blood*, 72, 1944–1949 (1988)]. Since the success of many chemotherapeutic drugs depends on the fact that neoplastic cells cycle more actively than normal cells, SCF alone or in combination with other factors acts as a growth factor for neoplastic cells and sensitizes them to the toxic effects of chemotherapeutic drugs.

Delivery Device

Figure 10:
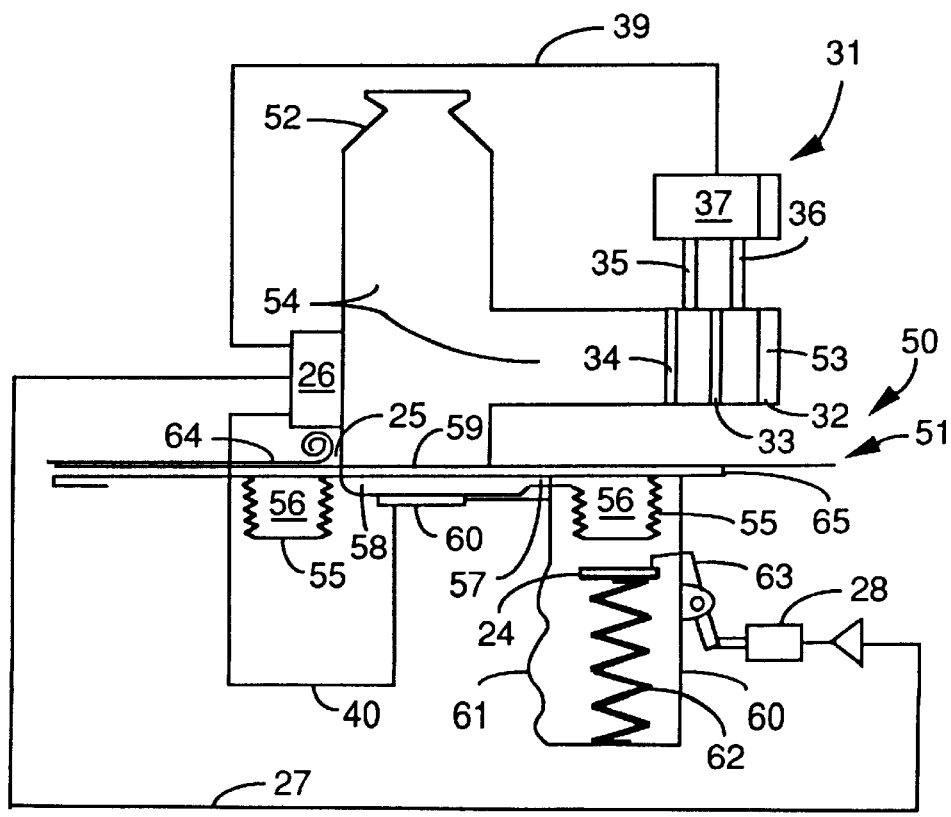

There are two preferred types of devices which can be used with the present invention. In general, one type uses a low boiling point propellant and the other uses aqueous formulations. The devices which use low boiling point propellants are shown in FIGS. 1–4 and an embodiment of a device which uses aqueous formulations is shown in FIG. 10. Regardless of which type is used the device is a hand-held, portable device which is comprised of (a) a means for separately measuring and analyzing the inspiratory flow rate and inspiratory volume of a patient and (b) a means for automatically releasing a measured amount of a drug into the inspiratory flow path of a patient, e.g. an automatic valve actuation means or mechanism for moving formulation through a porous membrane. In order to use the device, the device must be "loaded", i.e. connected to (c) a source of drug which, in general, is formulated in water or in a low boiling point propellant. The entire device is light weight (less than 1 kg preferable less than 0.5 kg loaded) and portable.

A formulation of a hematopoietic drug in a low boiling point propellant is typically contained in a pressurized canister which is connectable to the "unloaded" device, i.e., the device without the container. When the container of propellant and hematopoietic drug is connected to the device, the container will include a valve opening at one end which opening is seated into a flow path within the device. The device preferably includes a mouth piece at the end of the flow path, and the patient inhales from the mouth piece which causes an inspiratory flow to be measured within the flow path. This inspiratory flow causes an air flow transducer to generate a signal. This signal is conveyed to a microprocessor which is able to convert, continuously, the signal from the transducer in the inspiratory flow path to a flow rate in liters per minute. The microprocessor can further integrate this continuous air flow rate signal into a representation of cumulative inspiratory volume. At an appropriate point in the inspiratory cycle, the microprocessor can send a signal to an actuation means. When the actuation means is signaled, it releases a valve allowing drug and propellant to escape into the inspiratory flow path of the device and ultimately into the patient's lungs. After being released, the drug and propellant will preferably pass through a nozzle prior to entering the inspiratory flow path of the device and thereafter the lungs and circulatory system of the patient.

It is important to note that the firing threshold of the device is not based on a single criterion such as the rate of air flow through the device or a specific time after the patient begins inhalation. The firing threshold is based on an analysis of the patient's inspiratory flow profile. This means that the microprocessor controlling the device takes into consideration the instantaneous air flow rate as well as the cumulative inspiratory flow volume when it determines the optimal point in the patient's inspiratory cycle which would be most preferable in terms of reproducibly delivering the same amount of drug to the patient with each release of drug. The high degree of dosing repeatability needed to deliver hematopoietic drugs may be obtained merely by measuring and releasing at the same measured flow rate and volume for each release of drug. Further, the device preferably includes a means for recording a characterization of the inspiratory flow profile for the patient which is possible by including a microprocessor in combination with a read/write memory means and a flow measurement transducer. By using such devices, it is possible to change the firing threshold at any time in response to an analysis of the patient's inspiratory flow profile, and it is also possible to record drug dosing events over time.

FIG. 1 shows a cross-sectional view of a hand-held, portable, electronic breath-actuated inhaler device which can be used in connection with the present invention. The device is shown with a holder 1 having cylindrical side walls and a removable cap. The holder 1 is "loaded" in that it includes the pressurized canister 3. The canister 3 includes a non-metering valve 5 which is held down in the open position when the cap 2 is screwed down, thus setting the valve 5 into a seat 6 which is in connection with a flow path 8.

A formulation 4 comprised of a hematopoietic drug such a commercially available EPO or G-CSF and a suitable propellant, such as a low boiling point propellant, is contained within the pressurized canister 3. Propellant and hematopoietic drug are released from the canister 3 via the electrically controlled solenoid 7. In that the valve 5 of the canister is continuously open, another valve, contained within solenoid 7, facilitates the release of the drug. When the solenoid 7 allows release of propellant and drug, the propellant and drug flows through the flow path 8 and then through the solenoid actuated valve 9 into the flow path 10, out through the nozzle 13 and then into the inspiratory flow path 11 surrounded by walls 12.

It is important to note that a variety of devices can be used in order to carry out the hematopoietic therapy delivery methodology of the present invention. However, the device must be capable of allowing the release of a metered amount of hematopoietic drug based on pre-programmed criteria relating to flow rate and volume. These measurements may be made mechanically but are preferable electronic and are readable by the microprocessor 22. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, microprocessor 22, containing read only memory which in turn contains the pre-programmed information, is plugged into the device. For each of these three embodiments, changing the programming of the memory device readable by microprocessor 22 will radically change the behavior of the device by causing microprocessor 22 to be programmed in a different manner. As regards the present invention, the non-volatile memory contains information relevant only to the administration of a specific hematopoietic drug such as recombinately produced EPO hormone. Microprocessor 22 sends signals to solenoid 7 which determines the amount of drug delivered into the inspiratory flow path. Further, microprocessor 22 keeps a record of all drug dosing times and amounts using a read/write non-volatile memory which is in turn readable by an external device. The formulation 4 contained within canister 3 is released into the atmosphere ultimately via nozzle 13 which opens into inspiratory flow path 11. It is at this point that the low boiling point propellant within formulation 4 flashes, i.e. rapidly evaporates, thus providing particles of hematopoietic drug in an aerosol which is introduced into the mouth and then into the lungs of the patient. In order to allow for ease of use, it is possible to form inspiratory flow path 11 into a mouth piece which can be specifically designed to fit the mouth of a particular patient using the device.

The solenoid 7, and associated valve 9, flow paths 8 and 10, as well as nozzle 13 make up the aerosol delivery system 14 shown by the dotted lines within FIG. 1. The system 14 is in connection with the flow sensor 15 which is capable of measuring a flow rate of about 0 to about 300 liters per minute. The flow sensor 15 includes screens 16, 17 and 18 which are positioned approximately ¼ apart from each other. Tubes 19 and 20 open to the area between the screens 16, 17 and 18 with the tubes 19 and 20 being connected to a conventional differential pressure transducer 21. When the user draws air through inspiratory flow path 11, air is passed through the screens 16, 17 and 18 and the air flow can be measured by the differential air pressure transducer 21. The flow sensor 15 is in connection with the aerosol delivery system 14, and when a threshold value of air flow is reached, the aerosol delivery system 14 allows the release of formulation 4 so that a controlled amount of peptide drug is delivered to the patient. Solenoid 7 is connected to a microprocessor 22 via an electrical connection. The details of the microprocessor and the details of other drug delivery devices which might be used in connection with the present invention are described and disclosed within U.S. patent application Ser. No. 07/664,758, filed on Mar. 5, 1991 entitled "Delivery of Aerosol Medications for Inspiration" which application is incorporated in its entirety herein by reference, and it is specifically incorporated in order to describe and disclose devices as shown within FIG. 1 and the microprocessor and program technology used therewith.

Figure 2:
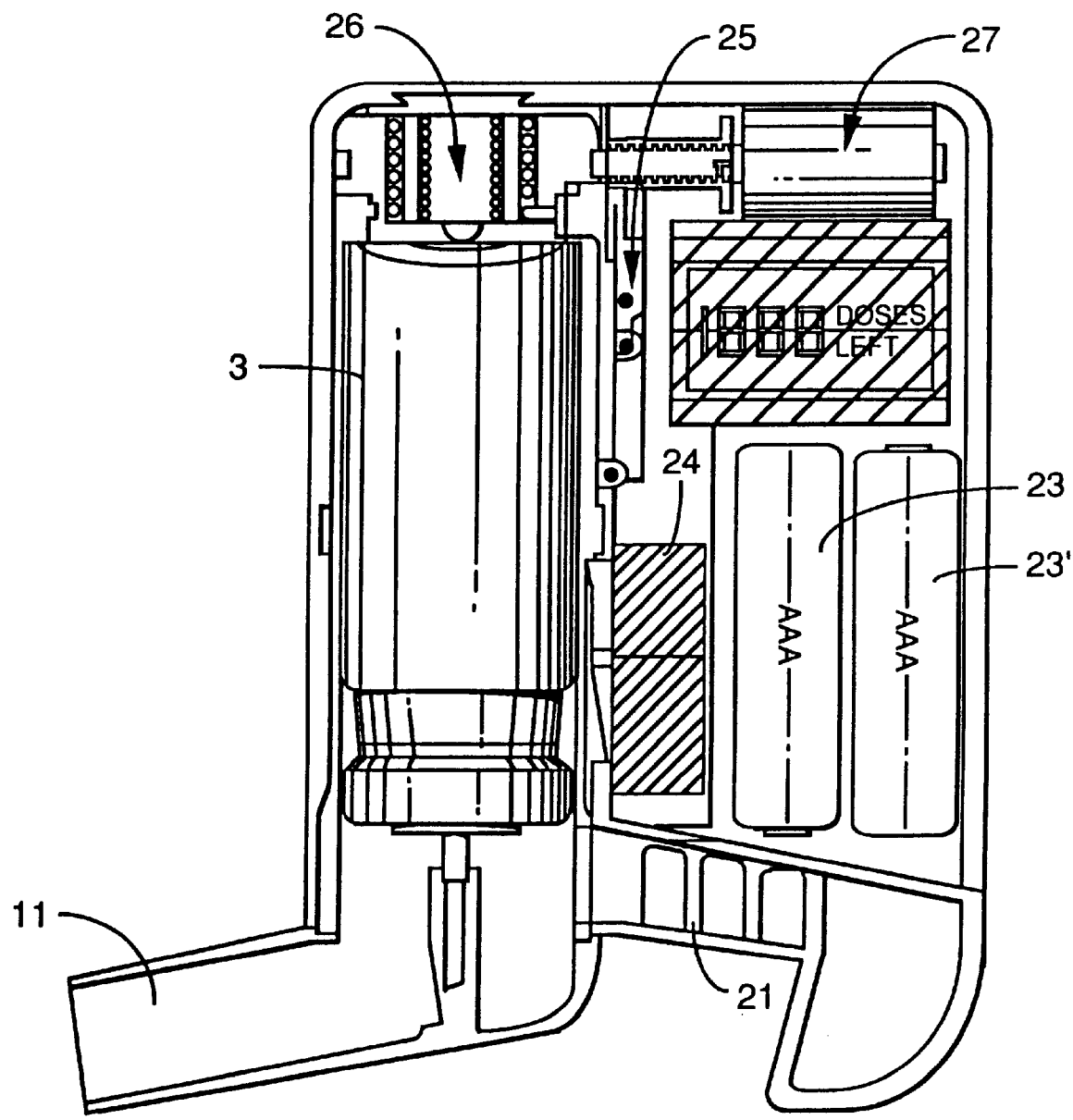

A cross-sectional view of yet another (and more preferred) embodiment of the hand-held, electronic, breath-actuated inhaler device of the invention is shown in FIG. 2. The device of FIG. 2 shows all of the components present within the single hand-held, portable device, i.e. the power source not shown in FIG. 1 is shown in the device in FIG. 2. Like the device shown within FIG. 1, the device of FIG. 2 includes a canister 3 which includes a canister valve 5. However, unlike the device of FIG. 1, the device of FIG. 2 does not have the valve continuously open but allows a valve 5 connected to the canister 3 to be opened by the mechanical force generated by a valve actuation mechanism 26 which is a motor driven, mechanical mechanism powered by a power source such as batteries 23 and 23'. However, like the device shown within FIG. 1, the patient inhales through inspiratory flow path 11 which can form a mouth piece in order to obtain a metering event using the differential pressure transducer 21. Further, when the inspiratory flow meets a threshold of a pre-programmed criteria, the microprocessor 24 sends a signal to an actuator release mechanism 25 which actuates the actuation mechanism 26 forcing canister 3 downward so that canister valve 5 releases formulation into the inspiratory flow path 11. Further details regarding the device of FIG. 2 are described within co-pending U.S. Pat. No. 5,394,866 entitled "An Automatic Aerosol Medication Delivery System and Methods" which is incorporated herein by reference in its entirety and specifically incorporated in order to describe and disclose devices as shown within FIG. 2 and the microprocessor and program technology used therewith.

Microprocessor 24 of FIG. 2 includes an external non-volatile read/write memory subsystem, peripheral devices to support this memory system, reset circuit, a clock oscillator, a data acquisition subsystem and an LCD annunciator subsystem. The discrete components are conventional parts which have input and output pins configured in a conventional manner with the connections being made in accordance with instructions provided by the device manufacturers. The microprocessor used in connection with the device of the invention is designed and programmed specifically so as to provide controlled and repeatable amounts of peptide drug to a patient upon actuation. Adjustments can be made in the program so that when the patient's inspiratory flow profile is changed such is taken into consideration. This can be done by allowing the patient to inhale through the device as a test in order to measure air flow with preferred drug delivery points determined based on the results of several inhalations by each particular patient. This process can be readily repeated when the inspiratory flow profile is changed for whatever reason, e.g. abdominal incisional pain resulting in low tidal volumes. Determination of optimal drug delivery points in the inspiratory flow can be done at each dosing event, daily, weekly, or with the replacement of a new canister in the device.

The microprocessor of the present invention, along with its associated peripheral devices, can be programmed so as to prevent the release of drug from the canister from occurring more than a given number of times within a given period of time. This feature makes it possible to prevent overdosing the patient. The overdose prevention feature can be particularly designed with each individual patient in mind or designed with particular groups of patients in mind.

The microprocessor of the present invention is programmed so as to allow for monitoring and recording data from the inspiratory flow monitor without delivering drug. This is done in order to characterize the patient's inspiratory flow profile in a given number of monitoring events, which monitoring events preferably occur prior to dosing events.

After carrying out a monitoring event, the preferred point within the inspiratory cycle for drug delivery can be calculated. This calculated point is a function of measured inspiratory flow rate as well as calculated cumulative inspiratory flow volume. This information is stored and used to allow activation of the valve when the inhalation cycle is repeated during the dosing event. The devices of FIGS. 1 and 2 have been put forth in connection with devices which use a low boiling point propellant and preferably use that propellant in combination with a suspension formulation which includes the dry powdered peptide drug within the low-boiling-point propellant. Those skilled in the art will readily recognize that such devices can be used for administering a solution of drug within the low-boiling-point propellant. However, those skilled in the art will also readily recognize that different mechanisms will be necessary in order to deliver different formulations, such as a dry powder without any propellant. A device could be readily designed so as to provide for the mechanical movement of a predetermined amount of dry powder to a given area. The dry powder would be concealed by a gate, which gate would be opened in the same manner described above, i.e., it would be opened when a predetermined flow rate level and cumulative volume have been achieved based on an earlier monitoring event. Patient inhalation would then cause the dry powder to form a dry dust cloud and be inhaled. Dry powder can also be aerosolized by compressed gas, and a solution can be aerosolized by a compressed gas released in a similar manner and then inhaled.

Aqueous System Device

The device of FIGS. 1 and 2 can be used to deliver a formulation of hematopoietic drug and low boiling point propellant. The system shown in FIG. 10 is used to deliver a formulation of hematopoietic drug in a carrier of water and/or ethanol. An embodiment of such a device will now be described in detail.

The device 50 shown in FIG. 10 is loaded with a disposable package 51. To use the device 50 a patient (not shown) inhales air from the mouthpiece 52. The air drawn in through the opening 53 and flows through the flow path 54. The package 51 is comprised of a plurality of containers 55. Each container 55 includes a drug formulation 56 and is in fluid connection via a channel 57 with the cavity 58. The cavity 58 is covered by the porous membrane 59. A vibration device 60 may be positioned directly below the cavity 58.

The device 50 is a hand-held, portable device which is comprised of (a) a device for holding a disposable package with at least one but preferably a number of drug containers, (b) a mechanical mechanism (e.g. piston or vibrator for moving the contents of a container (on the package) through a porous membrane (c) a device for measuring the inspiratory flow rate and separately determining the inspiratory volume of a patient, and (d) a switch for automatically releasing or firing the mechanical means after the inspiratory flow rate and/or volume reaches a predetermined point. If the device is electronic it also includes (e) a source of power.

The device for holding the disposable package may be nothing more than a narrow opening created between two outwardly extending bars or may include additional components such as one or more wheels, sprockets or rollers notably mounted on the end(s) of such bars. The rollers may be spring mounted so as to provide constant pressure against the surface(s) of the package. The device may also include a transport mechanism which may include providing drive power to roller(s) so that when they are rotated, they move the package from one container to the next. A power source driving the roller(s) can be programmed to rotate the rollers only enough to move the package from one container to the next. In order to use the device, the device must be "loaded," i.e. connected to a package which includes drug dosage units having liquid, flowable formulations of pharmaceutically active drug therein. The entire device is self-contained, light weight (less than 1 kg preferably less than 0.5 kg loaded) and portable.

FIG. 10 shows a cross-sectional view of a hand held, self-contained, portable, breath-actuated inhaler device 50 which can be used in the method of the present invention. The device 50 is shown with a holder 60 having cylindrical side walls and a hand grip 61. The holder 2 is "loaded" in that it includes a package 51. The package 51 includes a plurality of containers 56 connected by a connecting member 65.

The embodiment shown in FIG. 10 is a simple version of a device 50 which may be manually actuated and loaded. More specifically, the spring 62 may be compressed by the user until it is forced down below the actuation mechanism 63. When the user pushes the actuation mechanism 63 the spring 62 is released and the mechanical means in the form of a plate 24 is forced upward against a container 56. When the container 56 is compressed its contents are forced out through the channel 57 and membrane 59 and aerosolized. Another container 56 shown to the left is unused. A top cover sheet 64 has been peeled away from the top of the membrane 59 by a peeling means 25. The embodiment of FIG. 10 could provide the same results as a conventional metered dose inhaler. However, the device of FIG. 10 would not require the use of low boiling point propellants such as low boiling point fluorocarbons. Numerous additional features and advantages of the present invention can be obtained by utilizing the monitoring and electronic components described below.

The device must be capable of aerosolizing drug formulation in a container and preferably does such based on pre-programmed criteria which are readable by the microprocessor 26. The details of the microprocessor 26 and the details of other drug delivery devices which include a microprocessor and pressure transducer of the type used in connection with the present invention are described and disclosed within U.S. patent application Ser. No. 07/664,758 filed on Mar. 5, 1991 entitled "Delivery of Aerosol Medications for Inspiration" which application is incorporated in its entirety herein by reference, and is specifically incorporated in order to describe and disclose the microprocessor and program technology used therewith. The use of such a microprocessor with a drug delivery device is disclosed in our earlier filed U.S. Pat. No. 5,394,866 incorporated herein by reference. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, microprocessor 26, containing read only memory which in turn contains the pre-programmed information, is plugged into the device. For each of these three embodiments, changing the programming of the memory device readable by microprocessor 26 will radically change the behavior of the device by causing microprocessor 26 to be programmed in a different manner. This is done to accommodate different peptide drugs.

Microprocessor 26 sends signals via electrical connection 27 to electrical actuation device 28 which actuates the means 63 which fires the mechanical plate 24 forcing drug formulation in a container 56 to be aerosolized so that an amount of aerosolized drug is delivered into the inspiratory flow path 54. The device 28 can be a solenoid, motor, or any device for converting electrical to mechanical energy. Further, microprocessor 26 keeps a record of all drug dosing times and amounts using a read/write non-volatile memory which is in turn readable by an external device. Alternatively, the device records the information onto an electronic or magnetic strip on the package 51. The recorded information can be read later by the care-giver to determine the effectiveness of the treatment. In order to allow for ease of use, it is possible to surround the inspiratory flow path 54 with a mouth piece 52.

The electrical actuation means 28 is in electrical connection with the flow sensor 31 which is capable of measuring a flow rate of about 0 to about 800 liters per minute. It should be noted that inhalation flow rates are less than exhalation rates, e.g. max for inhalation 200 lpm and 800 lpm for exhalation. The flow sensor 31 includes screens 32, 33 and 34 which are positioned approximately ¼" apart from each other.

Tubes 35 and 36 open to the area between the screens 32, 33 and 34 with the tubes 35 and 36 being connected to a conventional differential pressure transducer 37. Another transducer designed to measure outflow through the opening 38 is also preferably included or the flow sensor 31 is designed so that the same components can measure inflow and outflow. When the user draws air through inspiratory flow path 54, air is passed through the screens 32, 33 and 34 and the air flow can be measured by the differential air pressure transducer 37. Alternatively, other means to measure pressure differential related to air flow, such as a conventional measuring device in the air way, may be used. The flow sensor 31 is in connection with the electrical actuation means 28 (via the connector 39 to the processor 26), and when a threshold value of air flow is reached (as determined by the processor 26), the electrical actuation means 28 fires the release of a mechanical means 63 releasing the plate 24 which forces the release of formulation from a container 56 so that a controlled amount of drug is delivered to the patient. The microprocessor 26 is also connected via connector 40 to an optionally present vibrating device 60 which may be activated.

Vibration Device

The ultrasonic vibrations are preferably at right angles to the plane of the membrane 14 and can be obtained by the use of a piezoelectric ceramic crystal or other suitable vibration device 60. The vibrating device 60 in the form of a piezoelectric crystal may be connected to the porous membrane 59 by means of an attenuator horn or acoustic conduction mechanism, which when correctly matched with the piezoelectric crystal frequency, efficiently transmits ultrasonic oscillations of the piezoelectric crystal to the resonance cavity and the porous polycarbonate membrane and if sized correctly permits the ultrasonic energy to be focused in a polycarbonate membrane 59 allowing for maximum use of the energy towards aerosolizing the liquid formulation 56. The size and shape of the attenuator horn is not of particular importance. It is preferred to maintain a relatively small size in that the device is hand held. The components are chosen based on the particular material used as the porous material, the particular formulation used and with consideration of the velocity of ultrasonic waves through the membrane to achieve a harmonic relationship at the frequency being used.

A high frequency signal generator drives the piezoelectric crystal. This generator is capable of roducing a signal having a frequency of from about 800 kilohertz (Khz) to about 4,000 kilohertz. The power output required depends upon the amount of liquid being nebulized per unit of time and the area and porosity of the polycarbonate membrane used for producing the drug dosage unit and/or the efficiency of the connection.

Vibration is applied while the formulation 56 is being forced from the pores of the polycarbonate membrane 59. The formulation can be aerosolized with only vibration i.e., without applying pressure. Alternatively, when vibration is applied in certain conditions the pressure required for forcing the liquid out can be varied depending on the liquid, the size of the pores and the shape of the pores but is generally in the range of about one to 200 psi, preferably 50 to 125 psi and may be achieved by using a piston, roller, bellows, a blast of forced compressed gas, or other suitable device. The vibration frequency used and the pressure applied can be varied depending on the viscosity of the liquid being forced out and the diameter and length of the openings or pores. In general, the present invention does not create effective aerosols if the viscosity of the liquid is greater than about 50 centipoises.

When small aerosolized particles are forced into the air, the particles encounter substantial frictional resistance. This may cause particles to slow down more quickly than desired and may result in particles colliding into each other and combining, which is undesirable with respect to maintaining the preferred particle size distribution within the aerosol. In order to aid in avoiding the particle collision problem, it is possible to include a means by which air or any other gas is forced through openings as the aerosol is forced out of the porous membrane. Accordingly, an air flow is created toward the patient and away from the nozzle opening which carries the formed particles along and aids in preventing their collision with each other. The amount of gas forced from the openings will vary depending upon the amount of aerosol being formed. However, the amount of gas is generally five to two hundred times the volume of the liquid formulation within the container. Further, the flow velocity of the gas is generally about equal to the flow velocity of the aerosolized particles being forced from the nozzle. The shape of the container opening, the shape of the membrane covering that opening, as well as the positioning and angling of the gas flow and particle flow can be designed to aid in preventing particle collision. When the two flow paths are substantially parallel, it is desirable to shape the opening and matching membrane so as to minimize the distance between any edge of the opening and the center of the opening. Accordingly, it is not desirable to form a circular opening which would maximize the distance between the outer edges of the circle and the center of the circle, whereas it is desirable to form an elongated narrow rectangle. Using such a configuration makes it possible to better utilize the air flow relative to all of the particles being forced form the container. When a circular opening is used, particles which are towards the center of the circle may not be carried along by the air being forced from the openings and will collide with each other. The elongate rectangle could be formed in a circle, thereby providing an annular opening and air could be forced outward from the outer and inner edges of the circle formed. Further details regarding such are described in U.S. patent application Ser. No. 08/247,012 filed May 20, 1994 which is incorporated herein by reference to disclose and describe such.

Security Features

In that hematopoietic drugs can be toxic it is desirable to design devices and methodology so as to hinder access to unauthorized users such as children to the extent possible. The methodology and devices of the present invention do so in an number of specific ways.

The device shown within FIG. 2 is designed to be reusable. More specifically, the drug delivery device can be "loaded" with a cassette of the type shown within either of FIGS. 3 and 4. The cassette is comprised of an outer cover 30, a canister 3 and top nozzle piece 31. The components are shown in a disassembled state in FIG. 3. A different embodiment of such components are shown in an assembled state within FIG. 4.

Figures 3, 4:
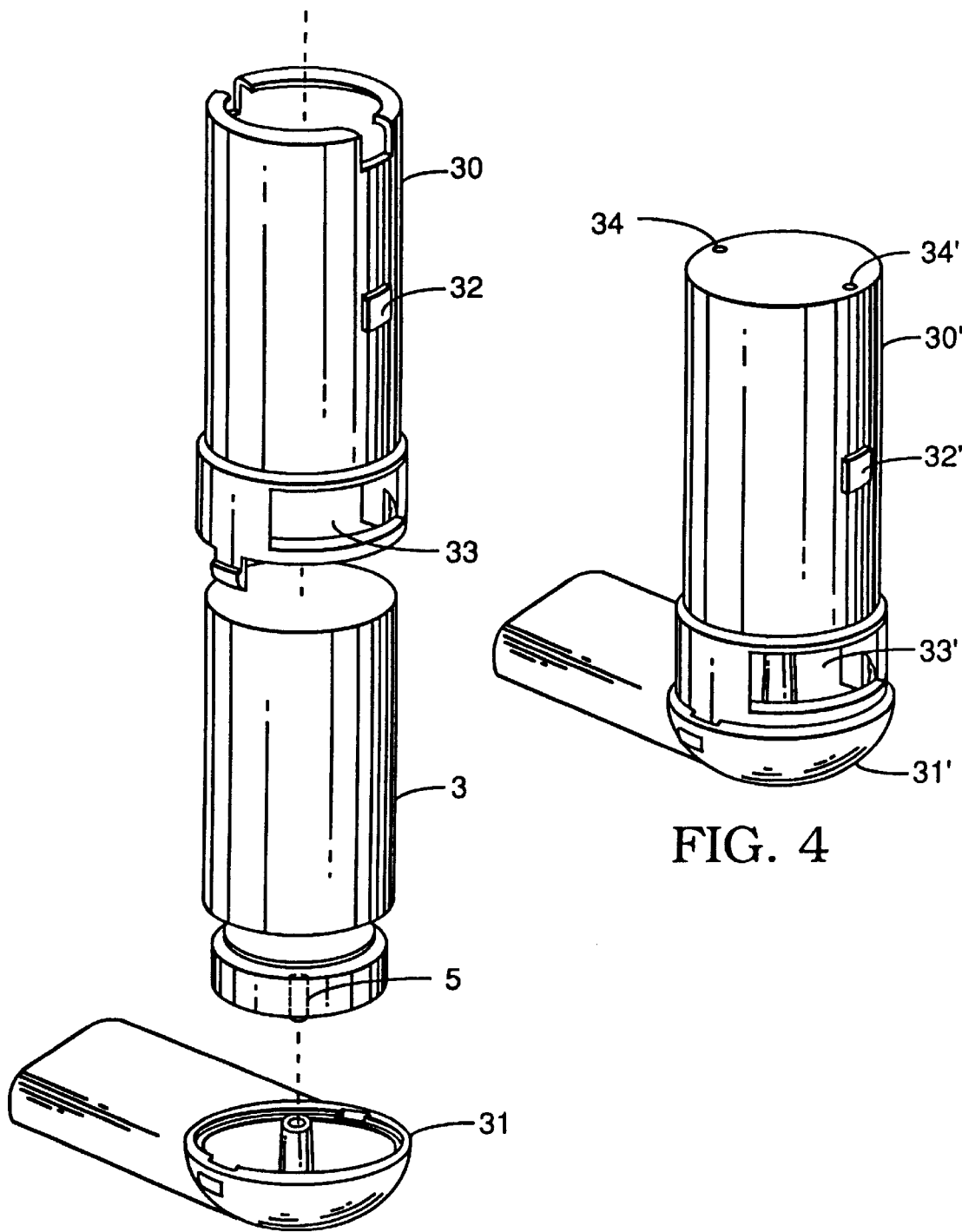

In essence, the cassette shown in FIG. 3 is somewhat less secure than the cassette shown within FIG. 4. As indicated, the top portion of the cover 30 is open within FIG. 3. This allows one to force the canister 3 downward and open the valve 5 to allow release of drug. However, in the embodiment shown in FIG. 4, there is no general opening but only two small openings 34 and 34'. Using the embodiment shown in FIG. 3, the cassette is loaded within the device shown in FIG. 2 and a motor driven piston forces the bottom of the canister 3 downward actuating the valve 5 to an open position. In accordance with the embodiment shown within FIG. 4, a two-pronged fork device is positioned over the end portion of the cover 30'. Each prong of the fork protrudes through an opening 34 and 34' allowing the canister 3 to be forced downward so that the valve 5 can be opened. It should be pointed out that when the cover 30 is attached to the top nozzle piece 31, they can be sealed together using a fast-acting glue or any appropriate means making it impossible to separate the components.

In that the hematopoietic drug is contained within the canister 3 with a low boiling point propellant it is extremely difficult to open the canister without losing all of the contents. Accordingly, the contents of the canister can generally be obtained only by including the canister within components 30 and 31 and attaching such to the device shown within FIG. 2.

The following description is provided with respect to FIG. 3 and the component shown therein, but is equally applicable with respect to FIG. 4 and the component shown therein. The cover 30 can have protuberances such as the protuberance 32 and openings such as the opening 33 thereon. These openings and protuberances can serve as a type of lock and key mechanism which is interactable with receiving protuberances and openings in the device shown in FIG. 2. Accordingly, unless the cover 30 includes the correct openings and protuberances in the correct position the cover will not fit into the device shown in FIG. 2 and cannot be operated. The body of the device as shown within FIG. 2 is designed so as to be capable of receiving the openings and protuberances on the cover 30. Thus, the cover 30 and receiving body portion on the device of FIG. 2 are designed so that they can be integrated but are also designed so that they will not integrate with other devices not specific for the delivery of a specific drug. Thus, as a first layer of security the device and methodology of the present invention provides for a physical lock and key interaction.

As a second line of defense against misuse of drugs, it is possible to design the components 31 and 32 and/or the device shown in FIG. 2 so as to receive a signal from a remote transmitter which is worn by the patient for which the drug was prescribed by the prescribing physician. By designing the device in this manner no drug can be released from the device unless the device is in close proximity to the intended user of the device.

It will, of course, be apparent to those skilled in the art that a combination of all or any of the above security features can be used. Further, the transmitting and receiving signals can be by any means of signalling and need not be limited to radio signals and thus could include infrared and other types of signals. Further, other interlocking mechanisms with more complex physical shapes could be readily devised in order to enhance the security of the device.

Hematopoietic Drug Containing Package

A package 51 which includes containers 56 is shown within the FIG. 10. This type of package includes the hematopoietic drug formulation in a flowable form within the container 56. However, in another embodiment the drug component of the formulation is maintained in a dry state substantially free of water in one container while the liquid component of the formulation such as the water, ethanol or a mixture thereof is maintained in a separate container. Such a package is shown in FIG. 11.

Figure 11:
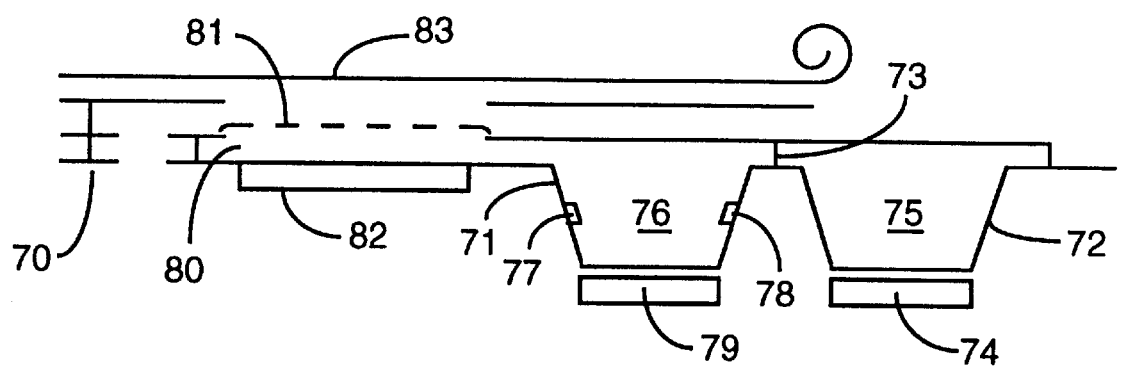

The package 70 of FIG. 11 includes a first container 71 and a second container 72. The containers 71 and 72 are in fluid connection with each other but the fluid connection is interrupted by a membrane 73 which membrane can be ruptured by the application of pressure in an amount of about 50 psi or less. A device such as the component 74 forces against the bottom of the container 72 and forces the contents 75 (which is liquid) against the membrane 73 which is then ruptured. The liquid 75 then enters the container 71 and mixes with the dry powder 76 present with the container 71. The container 71 may include mixing components 77 and 78. These components may be vibrating devices, ultrasonic devices or other suitable mechanisms allowing for the mixing of the liquid with the dry hematopoietic drug. When the mixing is completed the component 79 is forced against the container 71 forcing the drug formulation present therein into the chamber 80. Once the formulation is in the chamber 80 it is there under pressure and can be moved through the membrane 81 by the application of that pressure and/or by the use of a vibrating device 82. The formulation is moved through the membrane 81 only after removal of the cover sheet 83.

Package structures of the type shown within FIG. 11 are described within published PCT application US94/05825 incorporated herein by reference to disclose and describe such packages. The membrane 81 includes pores having a diameter in the range of about 0.25 micron to about 6 microns and a pore density in the range of $1 \times 10^4$ to about $1 \times 10^8$ pores per square centimeter. The porous membrane 81 is preferably comprised of a material having a density in the range of about 0.25 to 3.0 mg/cm$^2$, more preferably about 1.7 mg/cm$^2$ and a thickness of about 2 to about 20 microns, more preferably 8 to 12 microns. The liquid 75 present in the container 72 is preferably capable of dissolving the hematopoietic component 76. The hematopoietic drug powder 76 is preferably completely dissolved within the container 71 prior to being forced into the chamber 80. Dissolving the hematopoietic drug makes it easier to move the drug through the pores of the membrane 81 and create a fine mist aerosol. Keeping the dried hematopoietic drug powder apart from the liquid makes it possible to maintain a longer shelf life.

The instant invention is shown and described herein in which is considered to be the most practical and preferred embodiments. It is recognized, however, that the departures may be made therefrom which are within the scope of the invention and that obvious modifications will occur to one skilled in the art upon reading this disclosure.

I claim:

1. A method of administering a therapeutically effective amount of a hematopoietic drug to a patient with a handheld, self-contained, reusable device, the method comprising:

(a) determining the patient's inspiratory flow profile based on real time values of both said patient's inspiratory flow rate and inspiratory volume;

(b) determining a drug release point of said inspiratory flow profile, wherein at said drug release point said patient's inspiratory flow rate is in a range of about 0.10 to about 2.0 liters/second and inspiratory volume is in a range of about 0.15 to about 0.8 liters;

(c) releasing an aerosolized dose of a hematopoietic drug containing 100 to 1,000,000 units of drug in a 0.01 to 1 ml of drug formulation within the determined ranges of inspiratory flow rate and inspiratory volume combinations, wherein the aerosolized dose comprises aerosolized particles having a diameter in the range of 1.0 to 12.0 microns and is released from a package comprising a porous membrane with pores having a diameter in the range of 0.5 to 6.0 microns;

(d) repeating steps (a), (b) and (c) in a manner such that the releasing repeatedly occurs within substantially the same ranges of inspiratory flow rate and inspiratory flow volume combinations;

(e) monitoring the amount of drug released and preventing overdosing by preventing further release of drug beyond a given amount within a given period of time; and (f) providing a visual display to the patient of the amount of drug released.

2. The method of claim 1, wherein 20% or more of the released dose of aerosolized drug enters the circulatory system of the patient.

3. The method of claim 2, wherein 30% or more of the released dose of hematopoietic drug enters the circulatory system of the patient.

4. The method of claim 1, wherein the repeating of (d) is carried out until a therapeutically effective increase in the red blood cell level of the patient is obtained.

5. The method of claim 4, wherein the repeating of (d) is continuously carried out so as to obtain a red blood cell level in the range of about 3.9 to $6.0 \times 10^{-6}$ erythrocytes per microliter of blood.

6. The method of claim 1, further comprising:
   sending an audible signal to the patient at a predetermined time so as to prompt the patient to administer drug.

7. The method of claim 1, wherein the repeating of (c) is carried out over a period of time so as to maintain a desired drug to blood ratio in the patient.

8. The method of claim 1, wherein the hematopoietic drug is a non-naturally-occurring polypeptide having an amino acid sequence sufficiently duplicative of that of naturally-occurring stem cell factor to allow possession of a hematopoietic biological activity of naturally occurring stem cell factor.

9. The method of claim 1, wherein the hematopoietic drug is a combination of hIL-3 and hSCF.

10. The method of claim 1, wherein the hematopoietic drug is selected from the group consisting of CSF, EPO, G-CSF, CSF-1, IL-1, IL-2, IL-3, IL-4, IL-5, IL-6, IL-7, IL-8, IL-9, IL-10, IL-11, IGF-1, and LIF (leukemic Inhibitory Factor) and combinations thereof.

11. The method as claimed in claim 1, wherein the hematopoietic drug is isolated, purified, naturally-occurring human stem cell factor.

12. The method as claimed in claim 1, wherein the hematopoietic drug is a combination of hGM-CSF and hCSF.

13. The method as claimed in claim 1, wherein the amount of hematopoietic drug administered and time of administration is continually recorded and adjustments are made in the amount of drug administered based on the effect of drug administration on the red blood cell level of the patient.

14. The method as claimed in claim 1, wherein the hematopoietic drug is human recombinant EPO and is administered in an amount in the range of from about 50 to 100 U/kg of patient's body weight.

15. The method as claimed in claim 1, wherein the aerosolized dose includes 25 µl to 100 µl of formulation which dose contains 25,000 to 100,000 units of drug and is administered three times each week.

16. The method of claim 13, further comprising:
   retrieving the recorded information regarding the time and amount of hematopoietic drug administered; and
   analyzing the retrieved information to determine desired dosing levels for further administration of hematopoietic drug to the patient.

17. A method of administering a therapeutically effective amount of a hematopoietic drug to a patient with a hand-held, self-contained, reusable device, the method comprising:

(a) determining the patient's inspiratory flow profile;

(b) determining a drug release point of said inspiratory flow profile;

(c) releasing an aerosolized dose of a hematopoietic drug at said drug release point, wherein said aerosolized dose comprises aerosolized particles having a diameter in the range of 1.0 to 12.0 microns and is released from a disposable drug containing package comprising a porous membrane with pores having a diameter in the range of 0.5 to 6.0 microns; and (d) repeating steps (a) thru (c) in a manner such that the releasing repeatedly occurs at substantially said drug release point.

18. The method according to claim 17, wherein the inspiratory flow rate of said patient at said drug release point is in a range of about 0.10 to about 2.0 liters/second and the inspiratory volume of said patient at said drug release point is in a range of about 0.15 to about 0.8 liters.

* * * * *